(12) United States Patent
Watterson et al.

(10) Patent No.: US 10,212,994 B2
(45) Date of Patent: Feb. 26, 2019

(54) SMART WATCH BAND

(71) Applicant: ICON Health & Fitness, Inc., Logan, UT (US)

(72) Inventors: Scott R. Watterson, Logan, UT (US); Tony A. Smith, River Heights, UT (US)

(73) Assignee: ICON Health & Fitness, Inc., Logan, UT (US)

( * ) Notice: Subject to any disclaimer, the term of this patent is extended or adjusted under 35 U.S.C. 154(b) by 175 days.

(21) Appl. No.: 15/340,576

(22) Filed: Nov. 1, 2016

(65) Prior Publication Data

US 2017/0188668 A1 Jul. 6, 2017

Related U.S. Application Data

(60) Provisional application No. 62/249,819, filed on Nov. 2, 2015.

(51) Int. Cl.
| | |
|---|---|
| A44C 5/00 | (2006.01) |
| A44C 5/02 | (2006.01) |
| A44C 5/14 | (2006.01) |
| A43B 3/00 | (2006.01) |
| A61B 5/00 | (2006.01) |
| G04B 37/14 | (2006.01) |
| G04B 47/06 | (2006.01) |
| A61B 5/0205 | (2006.01) |
| A61B 5/024 | (2006.01) |
| A61B 5/11 | (2006.01) |

(52) U.S. Cl.
CPC .......... *A44C 5/0015* (2013.01); *A43B 3/0005* (2013.01); *A44C 5/0076* (2013.01); *A44C 5/027* (2013.01); *A44C 5/14* (2013.01); *A61B 5/0205* (2013.01); *A61B 5/02438* (2013.01); *A61B 5/11* (2013.01); *A61B 5/681* (2013.01); *G04B 37/1486* (2013.01); *G04B 47/063* (2013.01); *A61B 5/1123* (2013.01); *A61B 5/4866* (2013.01)

(58) Field of Classification Search
CPC ..... A44C 5/0015; A44C 5/0076; A44C 5/027; A44C 5/14; A43B 3/0005; A61B 5/0205; A61B 5/02438; A61B 5/11; A61B 5/681; A61B 5/1123; A61B 5/4866; G04B 37/1486; G04B 47/063
USPC ........................................................ 368/282
See application file for complete search history.

(56) References Cited

U.S. PATENT DOCUMENTS

| | | |
|---|---|---|
| 571,761 A | 11/1896 | Gulliford |
| 598,965 A | 2/1898 | Thompson |
| 624,995 A | 5/1899 | Tellefsen |
| 682,988 A | 9/1901 | Carroll |
| 785,319 A | 3/1905 | Miller et al. |
| 1,224,387 A | 5/1917 | Lane |
| 1,224,410 A | 5/1917 | Porte |
| 1,394,101 A | 10/1921 | Dodge |
| 1,579,886 A | 4/1926 | Oxner |
| 1,585,748 A | 5/1926 | Wendelken |
| 1,645,487 A | 10/1927 | Harling |
| 1,671,744 A | 5/1928 | Hoffmann |
| 1,730,309 A | 10/1929 | Miller |
| 1,747,721 A | 2/1930 | Lowman |
| 1,755,205 A | 4/1930 | Christensen |

(Continued)

*Primary Examiner* — Edwin A. Leon
(74) *Attorney, Agent, or Firm* — Ray Quinney & Nebeker

(57) ABSTRACT

A replacement wrist band may include a display and at least one replaceable module formed on the wrist band itself.

20 Claims, 12 Drawing Sheets

(56) References Cited

U.S. PATENT DOCUMENTS

| | | |
|---|---|---|
| 1,902,412 A | 3/1933 | Allen |
| 1,982,872 A | 12/1934 | Newton |
| 2,077,233 A | 4/1937 | Greenhill |
| 2,129,262 A | 9/1938 | Cole |
| 2,131,570 A | 9/1938 | Riley |
| 2,183,345 A | 12/1939 | Brandon |
| 2,324,970 A | 7/1943 | Woolley |
| 2,339,356 A | 1/1944 | Sachs |
| 2,381,149 A | 8/1945 | Wenneborg |
| 2,455,274 A | 11/1948 | Scriver |
| 2,493,205 A | 1/1950 | Hyman |
| 2,521,530 A | 9/1950 | Mcguffage |
| 2,533,341 A | 12/1950 | Alfano |
| 2,587,707 A | 3/1952 | Dever |
| 2,599,253 A | 6/1952 | Gits |
| 2,629,981 A * | 3/1953 | Melik-Minassiantz ............... G04B 37/1486 224/164 |
| 2,668,055 A | 2/1954 | Sharp |
| 2,680,022 A | 6/1954 | Walden |
| 2,688,960 A | 9/1954 | Fischer et al. |
| 2,707,465 A | 5/1955 | Nemeth |
| 2,714,007 A | 7/1955 | Jordan |
| 2,764,859 A | 10/1956 | Hanselmann |
| 2,829,891 A | 4/1958 | Ludwig |
| 2,829,892 A | 4/1958 | Ludwig |
| 2,900,493 A | 8/1959 | Cheng |
| 2,920,418 A | 1/1960 | Britt |
| 2,941,801 A | 6/1960 | Pedersen |
| 2,944,816 A | 7/1960 | Dixon |
| 2,973,962 A | 3/1961 | Griffin |
| 2,978,243 A | 4/1961 | Gabrielson |
| 2,991,589 A | 7/1961 | Glass |
| 3,024,021 A | 3/1962 | Coplin |
| 3,086,775 A | 4/1963 | Albert |
| 3,184,234 A | 5/1965 | Struble |
| 3,211,453 A | 10/1965 | Williams |
| 3,233,896 A | 2/1966 | King |
| 3,268,225 A | 8/1966 | Kolbel |
| 3,271,030 A | 9/1966 | Mueller |
| 3,307,319 A | 3/1967 | Christensen et al. |
| 3,310,305 A | 3/1967 | Howe |
| 3,310,320 A | 3/1967 | Hanna |
| 3,356,367 A | 12/1967 | Tewksbury |
| 3,416,792 A | 12/1968 | Morgan |
| 3,419,267 A | 12/1968 | Stolle |
| 3,419,268 A | 12/1968 | Bellet |
| 3,421,163 A | 1/1969 | Stoughton |
| 3,427,019 A | 2/1969 | Brown |
| 3,427,026 A | 2/1969 | Mahoney |
| 3,438,627 A | 4/1969 | La Lanne |
| 3,441,271 A | 4/1969 | Palacios |
| 3,451,672 A | 6/1969 | Kazdan |
| 3,458,966 A | 8/1969 | Dunbar et al. |
| 3,488,049 A | 1/1970 | Sasser, Jr. |
| 3,491,998 A | 1/1970 | Goodwin |
| 3,507,494 A | 4/1970 | Finkel |
| 3,511,500 A | 5/1970 | Dunn |
| 3,586,321 A | 6/1971 | Gehrke |
| 3,589,715 A | 6/1971 | Mark |
| 3,589,720 A | 6/1971 | Agamian |
| 3,593,994 A | 7/1971 | Anbar |
| 3,598,404 A | 8/1971 | Bowman |
| 3,604,726 A | 9/1971 | Tracy |
| 3,614,097 A | 10/1971 | Blickman |
| 3,622,152 A | 11/1971 | Place |
| 3,627,314 A | 12/1971 | Brown |
| 3,641,601 A | 2/1972 | Sieg |
| 3,658,327 A | 4/1972 | Thiede |
| 3,664,334 A | 5/1972 | Oneil |
| 3,708,164 A | 1/1973 | Griffin |
| 3,716,229 A | 2/1973 | Van Der Cleyen et al. |
| 3,717,338 A | 2/1973 | Hughes |
| 3,752,475 A | 8/1973 | Ott |
| 3,758,107 A | 9/1973 | Potgieter |
| 3,759,511 A | 9/1973 | Zinkin |
| 3,767,190 A | 10/1973 | Biggerstaff |
| 3,792,860 A | 2/1974 | Selnes |
| 3,809,393 A | 5/1974 | Jones |
| 3,836,144 A | 9/1974 | Mahoney |
| 3,850,431 A | 11/1974 | Winans |
| 3,862,768 A | 1/1975 | England |
| 3,892,403 A | 7/1975 | Green |
| 3,892,404 A | 7/1975 | Martucci |
| 3,899,210 A | 8/1975 | Samhammer et al. |
| 3,924,819 A | 12/1975 | Lapinskas |
| 3,929,329 A | 12/1975 | Rivera |
| 3,934,873 A | 1/1976 | Griffin |
| 3,935,690 A | 2/1976 | Lea |
| 3,938,803 A | 2/1976 | Wilmoth |
| 3,961,787 A | 6/1976 | Studebaker |
| 3,965,506 A | 6/1976 | Marks |
| 3,967,820 A | 7/1976 | Harper |
| 3,968,620 A | 7/1976 | Keltner |
| 3,984,100 A | 10/1976 | Firster |
| 3,992,733 A | 11/1976 | Racine |
| 4,004,801 A | 1/1977 | Campanaro |
| 4,011,611 A | 3/1977 | Lederman |
| 4,016,707 A | 4/1977 | Puchosic |
| 4,027,888 A | 6/1977 | Wilcox |
| 4,037,834 A | 7/1977 | Oaks |
| 4,059,265 A | 11/1977 | Wieder et al. |
| 4,065,124 A | 12/1977 | Egan |
| 4,066,868 A | 1/1978 | Witkin et al. |
| 4,067,078 A | 1/1978 | Winston |
| 4,068,846 A | 1/1978 | Forrest |
| 4,072,309 A | 2/1978 | Wilson |
| 4,093,224 A | 6/1978 | Hale |
| 4,101,124 A | 7/1978 | Mahnke |
| 4,103,889 A | 8/1978 | Lobur |
| 4,111,417 A | 9/1978 | Gardner |
| 4,116,434 A | 9/1978 | Bernstein |
| 4,132,404 A | 1/1979 | Wilson |
| 4,135,716 A | 1/1979 | Ginsburg |
| 4,147,353 A | 4/1979 | Moore |
| 4,159,826 A | 7/1979 | Hancock |
| 4,171,805 A | 10/1979 | Abbott |
| 4,176,836 A | 12/1979 | Coyle |
| 4,184,237 A | 1/1980 | Blankenship |
| 4,191,371 A | 3/1980 | Armer, Jr. |
| 4,199,136 A | 4/1980 | Mansfield |
| 4,202,581 A | 5/1980 | Fleishman |
| 4,212,480 A | 7/1980 | Mikina |
| 4,228,484 A | 10/1980 | Johnstone |
| 4,229,002 A | 10/1980 | Masters |
| 4,241,915 A | 12/1980 | Noble |
| 4,259,705 A | 3/1981 | Stifter |
| 4,263,682 A | 4/1981 | Bejarano |
| 4,274,625 A | 6/1981 | Gaetano |
| 4,274,632 A | 6/1981 | Jacobs |
| 4,285,516 A | 8/1981 | Southerland |
| 4,290,600 A | 9/1981 | Kolbel |
| 4,327,046 A | 4/1982 | Davis et al. |
| 4,327,908 A | 5/1982 | James |
| 4,336,933 A | 6/1982 | Appelbaum |
| 4,337,942 A | 7/1982 | Sidlinger et al. |
| 4,345,757 A | 8/1982 | Lo Voi |
| 4,351,525 A | 9/1982 | Rozenblad |
| 4,371,162 A | 2/1983 | Hartzell |
| 4,383,684 A | 5/1983 | Schliep |
| 4,386,915 A | 6/1983 | Gilliam |
| 4,390,204 A | 6/1983 | Fleishman |
| 4,412,751 A * | 11/1983 | Jeannet ............... G04G 17/083 368/204 |
| 4,418,514 A | 12/1983 | Spann |
| 4,429,871 A | 2/1984 | Flechner |
| 4,433,683 A | 2/1984 | McCoy et al. |
| 4,448,412 A | 5/1984 | Brentham |
| 4,463,948 A | 8/1984 | Mohr |
| 4,477,072 A | 10/1984 | Decloux |
| 4,489,933 A | 12/1984 | Fisher |
| 4,491,318 A | 1/1985 | Francke |
| 4,492,375 A | 1/1985 | Connelly |
| 4,505,477 A | 3/1985 | Wilkinson |

(56) References Cited

U.S. PATENT DOCUMENTS

| | | |
|---|---|---|
| 4,516,767 A | 5/1985 | Eskijian |
| 4,516,768 A | 5/1985 | Gallaro |
| 4,517,966 A | 5/1985 | Von Othegraven |
| 4,530,498 A | 7/1985 | Heatwole |
| 4,533,174 A | 8/1985 | Fleishman |
| 4,538,806 A | 9/1985 | Wilkerson |
| 4,564,193 A | 1/1986 | Stewart |
| 4,592,544 A | 6/1986 | Smith et al. |
| 4,601,469 A | 7/1986 | Sasser, Jr. |
| 4,627,619 A | 12/1986 | Rockwell et al. |
| 4,638,995 A | 1/1987 | Wilson |
| 4,640,268 A | 2/1987 | Roberts |
| 4,643,419 A | 2/1987 | Hyde |
| 4,645,198 A | 2/1987 | Levenston |
| 4,674,740 A | 6/1987 | Iams et al. |
| 4,700,947 A | 10/1987 | Heatwole |
| 4,707,759 A | 11/1987 | Bodkin |
| 4,720,112 A | 1/1988 | Stettner |
| 4,729,562 A | 3/1988 | Pipasik |
| 4,730,826 A | 3/1988 | Sudmeier |
| 4,739,436 A | 4/1988 | Stefani et al. |
| 4,739,986 A | 4/1988 | Kucharik |
| 4,744,558 A | 5/1988 | Smirmaul |
| 4,750,736 A | 6/1988 | Watterson |
| 4,759,542 A | 7/1988 | Hudec |
| 4,759,544 A | 7/1988 | Diaz |
| 4,762,319 A | 8/1988 | Krumholz |
| 4,768,778 A | 9/1988 | Thomas, Jr. |
| 4,778,173 A | 10/1988 | Joutras |
| 4,781,372 A | 11/1988 | Mccormack |
| 4,795,151 A | 1/1989 | Mulcaster |
| 4,799,475 A | 1/1989 | Iams et al. |
| 4,799,668 A | 1/1989 | Jansen |
| 4,801,140 A | 1/1989 | Bergeron |
| 4,804,179 A | 2/1989 | Murphy |
| 4,815,736 A | 3/1989 | Wright |
| 4,817,950 A | 4/1989 | Goo |
| 4,826,159 A | 5/1989 | Hersey |
| 4,826,166 A | 5/1989 | Baker et al. |
| 4,828,255 A | 5/1989 | Lahman |
| 4,841,713 A | 6/1989 | Beier |
| 4,844,187 A | 7/1989 | Jabero |
| 4,850,588 A | 7/1989 | Desjardins |
| 4,858,918 A | 8/1989 | Iams et al. |
| 4,861,023 A | 8/1989 | Wedman |
| 4,880,226 A | 11/1989 | Krantz |
| 4,880,230 A | 11/1989 | Cook |
| 4,883,272 A | 11/1989 | Lay |
| 4,893,809 A | 1/1990 | Blankenzee |
| 4,901,183 A | 2/1990 | Lee |
| 4,905,994 A | 3/1990 | Hartz |
| 4,911,430 A | 3/1990 | Flament |
| 4,911,438 A | 3/1990 | Van Straaten |
| 4,915,669 A | 4/1990 | Russell |
| 4,925,183 A | 5/1990 | Kim |
| 4,928,337 A | 5/1990 | Chauncey |
| 4,930,769 A | 6/1990 | Nenoff |
| 4,938,432 A | 7/1990 | Kurt et al. |
| 4,938,775 A | 7/1990 | Morgan |
| 4,942,505 A | 7/1990 | Maglica |
| 4,944,511 A | 7/1990 | Francis |
| 4,946,160 A | 8/1990 | Bertoletti |
| 4,948,149 A | 8/1990 | Lin |
| 4,949,954 A | 8/1990 | Hix |
| 4,958,832 A | 9/1990 | Kim |
| 4,963,798 A | 10/1990 | Mcdermott |
| 4,966,364 A | 10/1990 | Eggenberger |
| 4,971,316 A | 11/1990 | Dalebout et al. |
| 4,989,860 A | 2/1991 | Iams et al. |
| 5,000,444 A | 3/1991 | Dalebout et al. |
| 5,002,272 A | 3/1991 | Hofmeister |
| 5,007,632 A | 4/1991 | Wilkinson |
| 5,018,517 A | 5/1991 | Liardet |
| 5,024,441 A | 6/1991 | Rousseau |
| 5,029,848 A | 7/1991 | Sleamaker |
| 5,029,850 A | 7/1991 | Van Straaten |
| 5,044,632 A | 9/1991 | Jones |
| 5,048,823 A | 9/1991 | Bean |
| 5,062,624 A | 11/1991 | Reed |
| 5,062,629 A | 11/1991 | Vaughan |
| 5,078,393 A | 1/1992 | Morasiewicz |
| 5,080,353 A | 1/1992 | Tench |
| 5,083,797 A | 1/1992 | Vartija |
| 5,101,180 A | 3/1992 | Frey |
| 5,106,884 A | 4/1992 | Turner et al. |
| 5,108,095 A | 4/1992 | Nichols |
| 5,109,577 A | 5/1992 | Young |
| 5,112,045 A | 5/1992 | Mason et al. |
| 5,116,045 A | 5/1992 | Jahoda |
| 5,125,880 A | 6/1992 | Peters |
| 5,136,455 A | 8/1992 | Billingsley |
| 5,154,685 A | 10/1992 | Chen |
| 5,169,363 A | 12/1992 | Campanaro |
| 5,181,725 A | 1/1993 | Leras et al. |
| 5,190,504 A | 3/1993 | Scatterday |
| 5,190,506 A | 3/1993 | Zubik |
| 5,192,258 A | 3/1993 | Keller |
| 5,205,800 A | 4/1993 | Grant |
| 5,205,802 A | 4/1993 | Swisher |
| 5,224,909 A | 7/1993 | Hamilton |
| 5,226,866 A | 7/1993 | Engel et al. |
| 5,228,158 A | 7/1993 | Park |
| 5,234,395 A | 8/1993 | Miller et al. |
| 5,238,251 A | 8/1993 | Staka |
| 5,242,348 A | 9/1993 | Bates |
| 5,250,016 A | 10/1993 | Higgins |
| 5,251,961 A | 10/1993 | Pass |
| 5,256,127 A | 10/1993 | Yeh |
| 5,265,295 A | 11/1993 | Sturgis |
| 5,269,527 A | 12/1993 | Noval |
| 5,269,533 A | 12/1993 | Kellams |
| 5,271,616 A | 12/1993 | Grimaldi |
| 5,271,618 A | 12/1993 | Malwitz |
| 5,273,504 A | 12/1993 | Jones |
| 5,273,505 A | 12/1993 | Jones |
| 5,277,675 A | 1/1994 | Shifferaw |
| 5,277,684 A | 1/1994 | Harris |
| 5,279,533 A | 1/1994 | Yin et al. |
| 5,282,615 A | 2/1994 | Green et al. |
| 5,292,296 A | 3/1994 | Davignon |
| 5,293,307 A | 3/1994 | Maglica |
| 5,303,932 A | 4/1994 | Kessler |
| 5,308,075 A | 5/1994 | Theriault |
| 5,310,395 A | 5/1994 | Ko |
| 5,312,099 A | 5/1994 | Oliver, Sr. |
| 5,320,591 A | 6/1994 | Harmon et al. |
| 5,330,399 A | 7/1994 | Fan |
| 5,330,408 A | 7/1994 | Westmoreland, Jr. |
| 5,333,336 A | 8/1994 | Langsam |
| 5,342,274 A | 8/1994 | Hunker |
| 5,354,247 A | 10/1994 | Wilkinson |
| 5,354,251 A | 10/1994 | Sleamaker |
| 5,362,069 A | 11/1994 | Hall-Tipping |
| 5,362,295 A | 11/1994 | Nurge |
| 5,364,324 A | 11/1994 | Boettiger, Jr. |
| 5,370,594 A | 12/1994 | Grinblat |
| 5,376,053 A | 12/1994 | Ponder |
| 5,387,166 A | 2/1995 | Gvoich |
| 5,393,069 A | 2/1995 | Hearl |
| 5,399,140 A | 3/1995 | Klippel |
| 5,403,256 A | 4/1995 | Squires |
| 5,413,332 A | 5/1995 | Montgomery |
| 5,419,550 A | 5/1995 | Blom |
| 5,423,136 A | 6/1995 | Gulli |
| 5,429,567 A | 7/1995 | Gerschefske et al. |
| 5,433,438 A | 7/1995 | Gilman |
| 5,433,684 A | 7/1995 | Carrillo |
| 5,433,685 A | 7/1995 | Winslow |
| 5,435,799 A | 7/1995 | Lundin |
| 5,452,223 A | 9/1995 | Zuercher et al. |
| 5,452,896 A | 9/1995 | Core |
| 5,456,644 A | 10/1995 | Hecox et al. |
| 5,468,205 A | 11/1995 | McFall et al. |
| 5,472,390 A | 12/1995 | Faye |

(56) References Cited

U.S. PATENT DOCUMENTS

| | | |
|---|---|---|
| 5,474,509 A | 12/1995 | Hodgdon |
| 5,476,184 A | 12/1995 | Hill |
| 5,490,823 A | 2/1996 | Awbrey et al. |
| 5,496,235 A | 3/1996 | Stevens |
| 5,499,961 A | 3/1996 | Mattox |
| 5,518,476 A | 5/1996 | Mcleon |
| 5,518,483 A | 5/1996 | Oswald |
| 5,522,783 A | 6/1996 | Gordon |
| 5,527,249 A | 6/1996 | Harris |
| 5,530,633 A | 6/1996 | Yuen |
| 5,531,658 A | 7/1996 | Liao |
| 5,533,948 A | 7/1996 | Wilkinson |
| 5,536,226 A | 7/1996 | Gordon |
| 5,549,536 A | 8/1996 | Clark |
| 5,553,848 A | 9/1996 | Amron |
| 5,554,089 A | 9/1996 | Jones |
| 5,558,430 A | 9/1996 | Booty, Jr. |
| 5,562,572 A | 10/1996 | Carmein |
| 5,562,575 A | 10/1996 | Gvoich |
| 5,566,953 A | 10/1996 | Arriola et al. |
| 5,569,138 A | 10/1996 | Wang et al. |
| 5,573,485 A | 11/1996 | Geschwender |
| 5,575,738 A | 11/1996 | Millington et al. |
| 5,575,740 A | 11/1996 | Piaget |
| 5,577,981 A | 11/1996 | Jarvik |
| 5,577,987 A | 11/1996 | Brown |
| 5,580,321 A | 12/1996 | Rennhack |
| 5,582,565 A | 12/1996 | Soria |
| 5,584,787 A | 12/1996 | Guidry |
| 5,599,261 A | 2/1997 | Easley et al. |
| 5,603,334 A | 2/1997 | Sharp |
| 5,609,528 A | 3/1997 | Kehoe |
| 5,611,524 A | 3/1997 | Gordon |
| 5,620,069 A | 4/1997 | Hurwitz |
| 5,620,403 A | 4/1997 | Lundin |
| 5,624,358 A | 4/1997 | Hestilow |
| 5,624,360 A | 4/1997 | Wilkins |
| 5,630,661 A | 5/1997 | Fox |
| 5,637,057 A | 6/1997 | Collura |
| 5,637,065 A | 6/1997 | Chang |
| 5,643,154 A | 7/1997 | Awbrey |
| 5,643,161 A | 7/1997 | Gordon |
| 5,643,165 A | 7/1997 | Klekamp |
| 5,645,510 A | 7/1997 | Wilkinson |
| 5,649,884 A | 7/1997 | Manalo |
| 5,653,664 A | 8/1997 | Jennings |
| 5,654,857 A | 8/1997 | Gershen |
| 5,667,462 A | 9/1997 | Gordon |
| 5,667,464 A | 9/1997 | Simonson |
| 5,674,157 A | 10/1997 | Wilkinson |
| 5,674,167 A | 10/1997 | Piaget et al. |
| 5,681,250 A | 10/1997 | Hoover et al. |
| 5,683,337 A | 11/1997 | Zetocha |
| 5,690,387 A | 11/1997 | Sarti |
| 5,690,594 A | 11/1997 | Mankovitz |
| 5,692,995 A | 12/1997 | Alvarez et al. |
| 5,706,155 A | 1/1998 | Neiger et al. |
| 5,707,325 A | 1/1998 | Chiou |
| 5,709,634 A | 1/1998 | Pointer |
| 5,711,749 A | 1/1998 | Miller |
| 5,713,821 A | 2/1998 | Nissen |
| 5,718,655 A | 2/1998 | Phillips |
| 5,718,660 A | 2/1998 | Chen |
| 5,722,921 A | 3/1998 | Simonson |
| 5,722,922 A | 3/1998 | Watterson et al. |
| 5,725,444 A | 3/1998 | Heden |
| 5,728,050 A | 3/1998 | Lin |
| 5,730,442 A | 3/1998 | Anderson |
| 5,730,688 A | 3/1998 | Prusick |
| 5,733,012 A | 3/1998 | Jones |
| 5,735,776 A | 4/1998 | Swezey |
| 5,746,688 A | 5/1998 | Prager |
| 5,749,813 A | 5/1998 | Domzalski |
| 5,749,816 A | 5/1998 | Froelich, Sr. |
| 5,755,648 A | 5/1998 | Kildani |
| 5,755,651 A | 5/1998 | Homyonfer |
| 5,765,921 A | 6/1998 | Chuang |
| 5,766,119 A | 6/1998 | Clark |
| 5,769,759 A | 6/1998 | Alter |
| 5,772,543 A | 6/1998 | Paino |
| 5,772,563 A | 6/1998 | Lin |
| 5,776,034 A | 7/1998 | Stamler |
| 5,779,607 A | 7/1998 | Harris |
| 5,782,639 A | 7/1998 | Beal |
| 5,788,614 A | 8/1998 | Simonson |
| 5,788,617 A | 8/1998 | Paris |
| 5,792,031 A | 8/1998 | Alton |
| 5,803,841 A | 9/1998 | Daskoski |
| 5,810,698 A | 9/1998 | Hullett et al. |
| 5,813,932 A | 9/1998 | Grafton |
| 5,820,521 A | 10/1998 | Edwards et al. |
| 5,820,531 A | 10/1998 | Choi |
| 5,830,161 A | 11/1998 | Cosmano |
| 5,833,584 A | 11/1998 | Piaget et al. |
| 5,833,587 A | 11/1998 | Strong et al. |
| 5,835,321 A | 11/1998 | Elms et al. |
| 5,839,992 A | 11/1998 | Phillips |
| 5,842,938 A | 12/1998 | Garber |
| 5,853,352 A | 12/1998 | Login |
| 5,857,928 A | 1/1999 | Stewart |
| 5,860,897 A | 1/1999 | Gilbert et al. |
| 5,860,899 A | 1/1999 | Rassman |
| 5,863,278 A | 1/1999 | Chen |
| 5,865,714 A | 2/1999 | Marlowe |
| 5,868,651 A | 2/1999 | Washington |
| 5,878,551 A | 3/1999 | Curley et al. |
| 5,881,407 A | 3/1999 | Chu |
| 5,891,000 A | 4/1999 | Phillips |
| 5,895,342 A | 4/1999 | Solland |
| 5,897,474 A | 4/1999 | Romero |
| 5,899,835 A | 5/1999 | Puranda |
| 5,902,214 A | 5/1999 | Makikawa et al. |
| 5,902,220 A | 5/1999 | Lin |
| 5,906,564 A | 5/1999 | Jacobsen |
| 5,913,568 A | 6/1999 | Brightbill |
| 5,915,407 A | 6/1999 | West |
| 5,921,901 A | 7/1999 | Palacios |
| 5,938,571 A | 8/1999 | Stevens |
| 5,941,803 A | 8/1999 | Chamberlain |
| 5,963,406 A | 10/1999 | Neiger et al. |
| 5,967,952 A | 10/1999 | Bronstein et al. |
| 5,967,954 A | 10/1999 | Habing |
| 5,973,896 A | 10/1999 | Hirsh et al. |
| 5,976,039 A | 11/1999 | Epel et al. |
| 5,999,384 A | 12/1999 | Chen et al. |
| 6,012,188 A | 1/2000 | Daniels et al. |
| 6,012,993 A | 1/2000 | Guerriero |
| 6,013,011 A | 1/2000 | Moore et al. |
| 6,022,303 A | 2/2000 | Abdo |
| 6,024,677 A | 2/2000 | Siwertz |
| 6,027,435 A | 2/2000 | Nadorf |
| 6,042,518 A | 3/2000 | Hildebrandt et al. |
| 6,045,489 A | 4/2000 | Levine et al. |
| 6,053,829 A | 4/2000 | Conley |
| 6,062,702 A | 5/2000 | Krietzman |
| 6,063,007 A | 5/2000 | Sithole |
| 6,063,013 A | 5/2000 | Vathappallil |
| 6,068,580 A | 5/2000 | Myers |
| 6,071,213 A | 6/2000 | Raasch et al. |
| 6,071,217 A | 6/2000 | Barnett |
| 6,075,525 A | 6/2000 | Hsieh |
| 6,081,194 A * | 6/2000 | Sanchez ............ G08B 21/0453 340/573.1 |
| 6,086,218 A | 7/2000 | Robertson |
| 6,095,661 A | 8/2000 | Lebens et al. |
| 6,095,951 A | 8/2000 | Skowronski et al. |
| 6,106,437 A | 8/2000 | Brooks |
| 6,110,081 A | 8/2000 | Barrett |
| 6,120,424 A | 9/2000 | Arline |
| 6,123,647 A | 9/2000 | Mitchell |
| 6,132,338 A | 10/2000 | Shifferaw |
| 6,141,807 A | 11/2000 | Tapper |
| 6,142,405 A | 11/2000 | Black |
| 6,146,313 A | 11/2000 | Whan-Tong et al. |

(56) References Cited

U.S. PATENT DOCUMENTS

| | | |
|---|---|---|
| 6,149,555 A | 11/2000 | Kinback |
| 6,149,559 A | 11/2000 | Mackey |
| 6,158,874 A | 12/2000 | Brustein et al. |
| 6,162,061 A | 12/2000 | Taylor |
| 6,168,551 B1 | 1/2001 | Mcguinness |
| 6,174,269 B1 | 1/2001 | Eschenbach |
| 6,179,759 B1 | 1/2001 | Tellone |
| 6,183,397 B1 | 2/2001 | Stearns et al. |
| 6,186,662 B1 | 2/2001 | Jackson |
| 6,186,929 B1 | 2/2001 | Endelman et al. |
| 6,195,241 B1 | 2/2001 | Brooks et al. |
| 6,196,954 B1 | 3/2001 | Chen |
| 6,203,474 B1 | 3/2001 | Jones |
| 6,203,476 B1 | 3/2001 | Wang et al. |
| 6,210,348 B1 | 4/2001 | Reed |
| 6,213,923 B1 | 4/2001 | Cameron et al. |
| 6,213,924 B1 | 4/2001 | Kaiyoorawongs |
| 6,216,490 B1 * | 4/2001 | Radley-Smith ...... A44C 5/0015 345/56 |
| 6,217,483 B1 | 4/2001 | Kallassy |
| 6,220,974 B1 | 4/2001 | Moore |
| 6,220,990 B1 | 4/2001 | Crivello |
| 6,220,995 B1 | 4/2001 | Chen |
| 6,225,977 B1 | 5/2001 | Li |
| 6,229,679 B1 | 5/2001 | MacBeth |
| 6,231,489 B1 | 5/2001 | McBride et al. |
| 6,238,320 B1 | 5/2001 | Flanagan |
| 6,241,637 B1 | 6/2001 | Basyuk |
| 6,244,995 B1 | 6/2001 | Prsala |
| 6,248,047 B1 | 6/2001 | Abdo |
| 6,254,515 B1 | 7/2001 | Carman et al. |
| 6,259,996 B1 | 7/2001 | Haun et al. |
| 6,264,588 B1 | 7/2001 | Ellis |
| 6,278,596 B1 | 8/2001 | Simpson |
| 6,279,184 B1 | 8/2001 | George, II |
| 6,280,053 B1 | 8/2001 | Chien |
| 6,280,362 B1 | 8/2001 | Dalebout et al. |
| 6,280,366 B1 | 8/2001 | Hsieh |
| 6,288,882 B1 | 9/2001 | DiSalvo et al. |
| 6,306,109 B1 | 10/2001 | Polychronis |
| 6,309,331 B1 | 10/2001 | Raymond |
| 6,312,364 B1 | 11/2001 | Selsam |
| 6,312,366 B1 | 11/2001 | Prusick |
| 6,313,642 B1 | 11/2001 | Brooks |
| 6,328,675 B1 | 12/2001 | Kaye |
| 6,328,680 B1 | 12/2001 | Shifferaw |
| 6,334,227 B1 | 1/2002 | Larger |
| 6,348,026 B1 | 2/2002 | Kuo |
| 6,363,557 B2 | 4/2002 | Chou |
| 6,371,625 B2 | 4/2002 | Campman |
| 6,387,022 B1 | 5/2002 | Smith |
| 6,394,938 B1 | 5/2002 | Tornabene |
| 6,398,383 B1 | 6/2002 | Huang |
| 6,398,694 B1 | 6/2002 | Bountourakis |
| 6,400,104 B1 | 6/2002 | Ham |
| 6,413,194 B1 | 7/2002 | Gant |
| 6,413,197 B2 | 7/2002 | McKechnie et al. |
| 6,416,447 B1 | 7/2002 | Harmon |
| 6,419,611 B1 | 7/2002 | Levine et al. |
| 6,422,983 B1 | 7/2002 | Weck |
| 6,440,045 B1 | 8/2002 | Gaston |
| 6,447,424 B1 | 9/2002 | Ashby et al. |
| 6,464,999 B1 | 10/2002 | Huo et al. |
| 6,475,108 B1 | 11/2002 | Sarenana, Sr. |
| 6,478,699 B1 | 11/2002 | Fairweather |
| 6,482,128 B1 | 11/2002 | Michalow |
| 6,508,749 B1 | 1/2003 | Broadwater |
| 6,517,215 B2 | 2/2003 | Mele |
| 6,524,226 B2 | 2/2003 | Kushner |
| 6,532,613 B2 | 3/2003 | Berry, IV |
| 6,533,710 B2 | 3/2003 | Lin et al. |
| 6,544,153 B2 | 4/2003 | Lee |
| 6,547,706 B1 | 4/2003 | Chek |
| 6,551,215 B1 | 4/2003 | Gordon |
| 6,554,753 B1 | 4/2003 | Weck et al. |
| 6,569,066 B1 | 5/2003 | Patterson et al. |
| 6,575,884 B1 | 6/2003 | Eazor |
| 6,575,885 B1 | 6/2003 | Weck et al. |
| 6,585,627 B2 | 7/2003 | Fernandez |
| 6,595,905 B2 | 7/2003 | McBride |
| 6,598,993 B1 | 7/2003 | Dalton et al. |
| 6,599,222 B1 | 7/2003 | Wince |
| 6,602,171 B1 | 8/2003 | Tsen |
| 6,607,472 B2 | 8/2003 | Toole |
| 6,619,836 B1 * | 9/2003 | Silvant ............ G04G 17/08 368/281 |
| 6,634,996 B2 | 10/2003 | Jacobsen |
| 6,645,129 B2 | 11/2003 | Eschenbach |
| 6,652,421 B1 | 11/2003 | Chen |
| 6,659,914 B2 | 12/2003 | Plante |
| 6,663,498 B2 | 12/2003 | Stipan |
| 6,663,537 B2 | 12/2003 | McCoy |
| 6,676,576 B1 | 1/2004 | Wu |
| 6,676,577 B2 | 1/2004 | Stearns |
| 6,676,579 B1 | 1/2004 | Lin |
| 6,683,770 B1 | 1/2004 | Marsh |
| 6,688,753 B2 | 2/2004 | Calon et al. |
| 6,692,415 B1 | 2/2004 | Winston |
| 6,692,417 B2 | 2/2004 | Burrell |
| 6,699,162 B2 | 3/2004 | Chen |
| 6,702,726 B2 | 3/2004 | Lin |
| 6,709,126 B1 | 3/2004 | Leen |
| 6,709,371 B2 | 3/2004 | Wu |
| 6,716,144 B1 | 4/2004 | Shifferaw |
| 6,719,669 B1 | 4/2004 | Wang |
| 6,726,350 B1 | 4/2004 | Herold |
| 6,728,166 B2 * | 4/2004 | Grupp ............... A44C 5/0015 368/204 |
| 6,730,002 B2 | 5/2004 | Hald et al. |
| 6,732,391 B2 | 5/2004 | George, II |
| 6,740,008 B1 | 5/2004 | Ho |
| 6,746,372 B2 | 6/2004 | Hsu |
| 6,749,540 B1 | 6/2004 | Pasero et al. |
| 6,758,826 B2 | 7/2004 | Luettgen et al. |
| 6,764,431 B2 | 7/2004 | Yoss |
| 6,764,456 B1 | 7/2004 | Doherty |
| 6,767,314 B2 | 7/2004 | Thompson |
| 6,773,379 B1 | 8/2004 | Bing |
| 6,796,674 B2 | 9/2004 | Galli |
| 6,800,043 B1 | 10/2004 | Pohrer |
| 6,816,350 B1 | 11/2004 | Hoopes |
| 6,820,364 B1 | 11/2004 | Tyson |
| 6,824,265 B1 | 11/2004 | Harper |
| 6,837,833 B2 | 1/2005 | Elledge |
| 6,837,835 B2 | 1/2005 | Huang |
| 6,837,836 B2 | 1/2005 | Huang |
| 6,837,837 B2 | 1/2005 | Nethery |
| 6,837,838 B2 | 1/2005 | List |
| 6,840,652 B1 | 1/2005 | Hymer |
| 6,850,394 B2 | 2/2005 | Kim |
| 6,872,175 B2 | 3/2005 | Lin |
| 6,900,972 B1 | 5/2005 | Chan et al. |
| 6,902,515 B2 | 6/2005 | Howell et al. |
| 6,921,006 B2 * | 7/2005 | Bauer ................. A44C 5/16 224/164 |
| 6,937,455 B2 | 8/2005 | Krichtafovitch et al. |
| 6,942,487 B2 | 9/2005 | Corbalis |
| 6,942,605 B2 | 9/2005 | Baatz |
| 6,945,912 B2 | 9/2005 | Levi |
| 6,945,920 B1 | 9/2005 | Kemery et al. |
| 6,951,403 B2 | 10/2005 | Bennett |
| 6,952,906 B2 | 10/2005 | Nelson |
| 6,953,260 B1 | 10/2005 | Allen |
| 6,957,897 B1 | 10/2005 | Nelson et al. |
| 6,966,871 B2 | 11/2005 | Parmater |
| 6,966,872 B2 | 11/2005 | Eschenbach |
| 6,971,977 B2 | 12/2005 | Chen |
| 6,979,099 B2 | 12/2005 | Harris, Jr. |
| 6,979,285 B2 | 12/2005 | Lovison |
| 6,997,857 B2 | 2/2006 | Bowman et al. |
| 7,003,435 B2 | 2/2006 | Kolker et al. |
| 7,007,330 B2 | 3/2006 | Kuiper et al. |
| 7,008,084 B2 | 3/2006 | Galli |
| 7,008,359 B2 | 3/2006 | Fan et al. |

(56) References Cited

U.S. PATENT DOCUMENTS

| | | |
|---|---|---|
| 7,011,310 B2 | 3/2006 | Rowan |
| 7,021,630 B1 | 4/2006 | Cho |
| 7,041,041 B1 | 5/2006 | Evans |
| 7,052,440 B2 | 5/2006 | Pyles et al. |
| 7,059,744 B2 | 6/2006 | Sharrah |
| 7,068,480 B2 | 6/2006 | Wong et al. |
| 7,083,299 B2 | 8/2006 | Chapman |
| 7,083,536 B2 | 8/2006 | Lu et al. |
| 7,094,185 B2 | 8/2006 | Greenland |
| 7,111,958 B2 | 9/2006 | Coman |
| 7,112,168 B2 | 9/2006 | Dalebout et al. |
| 7,125,371 B2 | 10/2006 | Henderson |
| 7,128,701 B1 | 10/2006 | Ketcham |
| 7,136,265 B2 | 11/2006 | Wong et al. |
| 7,137,933 B2 | 11/2006 | Shifferaw |
| 7,149,065 B2 | 12/2006 | Baldwin et al. |
| 7,175,573 B1 | 2/2007 | Huang |
| 7,179,212 B2 | 2/2007 | Hsiung et al. |
| 7,186,206 B2 | 3/2007 | Wren |
| 7,204,790 B2 | 4/2007 | Sleamaker |
| 7,213,743 B2 | 5/2007 | Carlson et al. |
| 7,226,373 B2 | 6/2007 | Arenas |
| 7,229,043 B2 | 6/2007 | Pitcher |
| 7,232,404 B2 | 6/2007 | Nelson |
| 7,244,217 B2 | 7/2007 | Rodgers, Jr. |
| 7,244,220 B2 | 7/2007 | Carney |
| 7,270,628 B2 | 9/2007 | Campanaro |
| 7,278,955 B2 | 10/2007 | Giannelli et al. |
| 7,283,340 B1 | 10/2007 | Finlay, Sr. et al. |
| 7,285,080 B1 | 10/2007 | Chiu |
| 7,291,101 B2 | 11/2007 | Deal |
| 7,297,079 B1 | 11/2007 | Delauter |
| 7,305,790 B2 | 12/2007 | Kay |
| 7,309,303 B1 | 12/2007 | Proctor |
| 7,322,907 B2 | 1/2008 | Bowser |
| 7,326,156 B2 | 2/2008 | Dworzan |
| 7,335,117 B2 | 2/2008 | Reason-Kerkhoff |
| 7,335,140 B2 | 2/2008 | Webber et al. |
| 7,335,146 B2 | 2/2008 | Gerstung |
| 7,342,360 B2 | 3/2008 | Van Deursen et al. |
| 7,344,266 B2 | 3/2008 | Coman |
| 7,347,581 B2 | 3/2008 | Krieger |
| 7,357,766 B2 | 4/2008 | Langer et al. |
| 7,359,121 B2 | 4/2008 | French et al. |
| 7,361,125 B2 | 4/2008 | Webber et al. |
| 7,361,127 B2 | 4/2008 | Tremayne |
| 7,364,517 B1 | 4/2008 | Johnsen |
| 7,364,538 B2 | 4/2008 | Aucamp |
| 7,374,522 B2 | 5/2008 | Arnold |
| 7,377,888 B2 | 5/2008 | Godbold |
| 7,381,168 B2 | 6/2008 | Bowser |
| 7,387,402 B1 | 6/2008 | Lui |
| 7,387,599 B1 | 6/2008 | Hsu |
| 7,393,120 B2 | 7/2008 | Kang et al. |
| 7,431,679 B1 | 10/2008 | Tageant |
| 7,448,497 B2 | 11/2008 | Muchin et al. |
| 7,455,633 B2 | 11/2008 | Brown et al. |
| 7,460,346 B2 | 12/2008 | Deshpande et al. |
| 7,478,878 B2 | 1/2009 | Oettinger |
| 7,481,753 B2 | 1/2009 | James et al. |
| 7,485,079 B2 | 2/2009 | Brown et al. |
| 7,487,932 B2 | 2/2009 | Ellis |
| 7,503,671 B2 | 3/2009 | Kang et al. |
| 7,510,214 B1 | 3/2009 | Oxford |
| 7,520,840 B2 | 4/2009 | Shifferaw |
| 7,537,552 B2 | 5/2009 | Dalebout et al. |
| 7,549,770 B2 | 6/2009 | Devaney |
| 7,549,958 B2 | 6/2009 | Hirata |
| 7,553,260 B2 | 6/2009 | Piaget et al. |
| 7,563,001 B2 | 7/2009 | Bobbin |
| 7,575,540 B1 | 8/2009 | Dobrow |
| 7,584,690 B2 | 9/2009 | Cauley |
| 7,585,263 B2 | 9/2009 | Brown et al. |
| 7,591,773 B2 | 9/2009 | Weir |
| 7,611,445 B2 | 11/2009 | Brown et al. |
| 7,614,978 B2 | 11/2009 | Piaget |
| 7,618,260 B2 * | 11/2009 | Daniel ................ A44C 5/0007 24/311 |
| 7,618,350 B2 | 11/2009 | Dalebout et al. |
| 7,621,858 B2 | 11/2009 | Sheron |
| 7,625,314 B2 | 12/2009 | Ungari |
| 7,625,317 B2 | 12/2009 | Stevenson |
| 7,635,195 B2 | 12/2009 | Tarter |
| 7,645,218 B2 | 1/2010 | Potok et al. |
| 7,645,221 B1 | 1/2010 | Curry |
| 7,651,446 B1 | 1/2010 | Eschenbach |
| 7,652,216 B2 | 1/2010 | Sharrah et al. |
| 7,658,700 B2 | 2/2010 | Maloy |
| 7,661,623 B2 | 2/2010 | Peng et al. |
| 7,662,076 B1 | 2/2010 | Ho |
| 7,666,120 B2 | 2/2010 | Stevenson |
| 7,666,126 B2 | 2/2010 | Rempe |
| 7,674,003 B2 | 3/2010 | Sharrah et al. |
| 7,682,290 B2 | 3/2010 | Liao et al. |
| 7,682,291 B2 | 3/2010 | Gill et al. |
| 7,691,041 B2 | 4/2010 | Abdo |
| 7,699,794 B2 | 4/2010 | Meyer et al. |
| 7,713,181 B1 | 5/2010 | Durham |
| 7,713,182 B2 | 5/2010 | Bizzell et al. |
| 7,722,506 B2 | 5/2010 | Pratson et al. |
| 7,722,509 B2 | 5/2010 | Eder |
| 7,722,513 B2 | 5/2010 | Habing |
| 7,731,637 B2 | 6/2010 | Eredita |
| 7,736,286 B2 | 6/2010 | Panaiotov |
| 7,758,469 B2 | 7/2010 | Dyer et al. |
| 7,771,076 B1 | 8/2010 | Mattheis |
| 7,775,952 B1 | 8/2010 | Curran et al. |
| 7,779,572 B2 | 8/2010 | Potterfield et al. |
| 7,780,585 B1 | 8/2010 | Rivas |
| 7,823,317 B2 | 11/2010 | Potterfield et al. |
| 7,833,132 B2 | 11/2010 | Hylbert et al. |
| 7,833,141 B2 | 11/2010 | Kulka |
| 7,833,143 B1 | 11/2010 | Tsai |
| 7,837,603 B1 | 11/2010 | Carnell, Sr. |
| 7,845,267 B2 | 12/2010 | Potterfield et al. |
| 7,845,820 B2 | 12/2010 | Bertken |
| 7,850,330 B2 | 12/2010 | Spartano et al. |
| 7,862,486 B1 | 1/2011 | Watson |
| 7,862,490 B2 | 1/2011 | Glynn |
| 7,878,957 B1 | 2/2011 | Chen |
| 7,894,888 B2 * | 2/2011 | Chan ................ A61B 5/0006 600/509 |
| 7,951,050 B2 | 5/2011 | Raumann |
| 7,954,272 B2 | 6/2011 | Potterfield et al. |
| 7,967,728 B2 | 6/2011 | Zavadsky |
| 7,993,253 B2 | 8/2011 | Fernandez |
| 7,997,021 B2 | 8/2011 | Cauley et al. |
| 7,997,755 B2 | 8/2011 | Liao |
| 7,997,770 B2 | 8/2011 | Meurer |
| 7,998,041 B1 | 8/2011 | Johnson |
| 8,002,282 B1 | 8/2011 | Koski |
| 8,002,648 B1 | 8/2011 | Quinn et al. |
| 8,007,413 B1 | 8/2011 | Wu |
| 8,012,071 B2 | 9/2011 | Grisdale |
| 8,043,199 B1 | 10/2011 | Barker |
| 8,057,329 B2 | 11/2011 | Cusimano |
| 8,062,196 B1 | 11/2011 | Khubani |
| 8,075,463 B2 | 12/2011 | Mills et al. |
| 8,113,682 B2 | 2/2012 | Bertken |
| 8,113,997 B2 | 2/2012 | Fernandez et al. |
| 8,118,715 B2 | 2/2012 | Greene et al. |
| 8,118,717 B1 | 2/2012 | Lai |
| 8,118,720 B2 | 2/2012 | Sebastian |
| 8,157,709 B2 | 4/2012 | Wilkinson |
| 8,167,777 B2 | 5/2012 | Nichols |
| 8,197,364 B2 | 6/2012 | Henkel |
| 8,206,272 B2 | 6/2012 | Greene |
| 8,206,275 B2 | 6/2012 | Chang |
| 8,246,405 B2 | 8/2012 | Checkley |
| 8,246,492 B2 | 8/2012 | Gangelhoff |
| 8,262,516 B2 | 9/2012 | Fuentes |
| 8,267,846 B2 | 9/2012 | Yang |
| 8,313,420 B2 | 11/2012 | Casha |
| 8,315,823 B2 | 11/2012 | Berme et al. |

(56) References Cited

U.S. PATENT DOCUMENTS

| | | |
|---|---|---|
| 8,323,154 B1 | 12/2012 | Bolillo |
| 8,353,808 B1 | 1/2013 | Barney |
| 8,360,596 B2 | 1/2013 | Bertken |
| 8,366,293 B2 | 2/2013 | Mcdermott |
| 8,414,461 B2 | 4/2013 | Wang |
| 8,465,403 B2 | 6/2013 | McCall, Jr. |
| 8,523,793 B1 | 9/2013 | Waldon, Sr. |
| 8,529,083 B1 | 9/2013 | Reed |
| 8,550,965 B2 | 10/2013 | Candela |
| 8,591,383 B1 | 11/2013 | McAlpin |
| 8,641,586 B2 | 2/2014 | Bremer |
| 8,641,588 B2 | 2/2014 | Verheem |
| 8,668,190 B1 | 3/2014 | Heruska et al. |
| 8,672,784 B2 | 3/2014 | Berggren et al. |
| 8,678,985 B2 | 3/2014 | Mattox |
| 8,706,530 B2 | 4/2014 | Dacadoo |
| 8,727,956 B2 | 5/2014 | Ho |
| 8,733,966 B2 | 5/2014 | Maglica et al. |
| 8,790,222 B2 | 7/2014 | Burger |
| 8,806,795 B1 | 8/2014 | Kay |
| 8,814,754 B2 | 8/2014 | Weast et al. |
| 8,814,764 B2 | 8/2014 | Vaughns |
| 8,814,767 B2 | 8/2014 | Brodbeck |
| 8,834,326 B1 | 9/2014 | Fulks |
| 8,860,713 B2 | 10/2014 | Katz et al. |
| 8,870,726 B2 | 10/2014 | Watterson et al. |
| 8,870,766 B2 | 10/2014 | Stivoric et al. |
| 8,884,752 B2 | 11/2014 | Tai et al. |
| 8,911,336 B2 | 12/2014 | Chiu |
| 8,926,459 B2 | 1/2015 | Berggren et al. |
| 8,931,201 B2 | 1/2015 | Gianladis et al. |
| 8,936,539 B2 | 1/2015 | Richard |
| 8,944,980 B2 | 2/2015 | Ho |
| 8,944,981 B2 | 2/2015 | Ho |
| 8,947,226 B2 | 2/2015 | Dugan |
| 8,948,832 B2 | 2/2015 | Hong et al. |
| 8,954,135 B2 | 2/2015 | Yuen et al. |
| 8,960,967 B2 | 2/2015 | Harwood |
| 8,979,298 B1 | 3/2015 | Wang |
| 8,992,392 B2 | 3/2015 | Giannelli et al. |
| 8,998,815 B2 | 4/2015 | Venkatraman et al. |
| 9,004,724 B2 | 4/2015 | Gao |
| 9,005,089 B2 | 4/2015 | Huang |
| 9,011,153 B2 | 4/2015 | Bennett et al. |
| 9,028,368 B2 | 5/2015 | Ashby et al. |
| 9,033,712 B2 | 5/2015 | Vasin |
| 9,039,581 B2 | 5/2015 | Chia et al. |
| 9,044,639 B2 | 6/2015 | Chia et al. |
| 9,074,739 B2 | 7/2015 | Deighton et al. |
| 9,079,056 B1 | 7/2015 | McAlpin |
| 9,079,067 B2 | 7/2015 | Huber et al. |
| 9,084,919 B2 | 7/2015 | Ross |
| 9,095,223 B2 | 8/2015 | Revell |
| 9,095,738 B2 | 8/2015 | Senegal |
| 9,095,740 B2 | 8/2015 | Wu |
| 9,151,561 B2 | 10/2015 | Morrow et al. |
| 9,180,337 B2 | 11/2015 | Chia et al. |
| 9,188,460 B2 | 11/2015 | Burton et al. |
| 9,205,298 B2 | 12/2015 | Hockridge et al. |
| 9,233,267 B2 | 1/2016 | Wilkins |
| 9,259,606 B2 | 2/2016 | Wolan |
| 9,274,506 B2 | 3/2016 | Lu |
| 9,295,870 B2 | 3/2016 | Mikulski |
| 9,314,681 B2 | 4/2016 | Palardis |
| 9,350,315 B1 | 5/2016 | Gonzalez Moreno |
| 9,364,706 B2 | 6/2016 | Lo |
| 9,387,363 B1 | 7/2016 | Polinsky |
| 9,446,285 B1 | 9/2016 | Drath |
| 9,474,923 B2 | 10/2016 | Davenport |
| 9,486,682 B2 | 11/2016 | Daugard |
| 9,529,966 B2 | 12/2016 | Weast et al. |
| 9,533,191 B2 | 1/2017 | Carbone |
| 9,536,449 B2 | 1/2017 | Connor |
| 9,572,745 B2 | 2/2017 | Lin |
| 9,586,090 B2 | 3/2017 | Watterson et al. |
| 9,597,546 B2 | 3/2017 | Maholmes |
| 9,599,632 B2 | 3/2017 | Yuen |
| 9,630,041 B2 | 4/2017 | Ellis |
| 9,649,521 B2 | 5/2017 | Miller et al. |
| 9,702,653 B2 | 7/2017 | Cauley, Jr. et al. |
| 9,707,433 B1 | 7/2017 | McGibbons |
| 9,734,477 B2 | 8/2017 | Weast et al. |
| 9,737,751 B2 | 8/2017 | Anderson |
| 9,744,394 B2 | 8/2017 | Frederick |
| 9,808,665 B1 | 11/2017 | Demarais et al. |
| 9,814,936 B1 | 11/2017 | Bucolo |
| 9,839,574 B2 | 12/2017 | Lawrie |
| 9,868,023 B2 | 1/2018 | Boykin |
| 9,868,024 B2 | 1/2018 | Castelluccio |
| 9,889,359 B2 | 2/2018 | Ouellette |
| 9,908,002 B2 | 3/2018 | Robertson |
| 9,914,014 B2 | 3/2018 | Lagree et al. |
| 9,968,814 B2 | 5/2018 | Miller et al. |
| 10,004,942 B1 | 6/2018 | Huang |
| 10,035,040 B2 | 7/2018 | Huber et al. |
| 2002/0077221 A1 | 6/2002 | Dalebout et al. |
| 2002/0099274 A1 | 7/2002 | Isomura et al. |
| 2002/0111109 A1 | 8/2002 | Kwan |
| 2002/0123416 A1 | 9/2002 | Huang |
| 2002/0124017 A1 | 9/2002 | Mault |
| 2002/0160891 A1 | 10/2002 | Gallagher |
| 2002/0193714 A1 | 12/2002 | Pecora |
| 2003/0017918 A1 | 1/2003 | Webb et al. |
| 2003/0022770 A1 | 1/2003 | Lee |
| 2003/0032533 A1 | 2/2003 | Hecox |
| 2003/0050156 A1 | 3/2003 | Tornabene |
| 2003/0066268 A1 | 4/2003 | George |
| 2003/0130100 A1 | 7/2003 | Perez |
| 2003/0158023 A1 | 8/2003 | Yu |
| 2004/0033848 A1 | 2/2004 | Bragg |
| 2004/0058781 A1 | 3/2004 | Plante |
| 2004/0077468 A1 | 4/2004 | Myles |
| 2004/0087420 A1 | 5/2004 | Montesquieux |
| 2004/0147331 A1 | 7/2004 | Feller |
| 2004/0266593 A1 | 12/2004 | Schwendeman |
| 2005/0002186 A1 | 1/2005 | Krieger et al. |
| 2005/0075223 A1 | 4/2005 | Wu |
| 2005/0085348 A1 | 4/2005 | Kiefer |
| 2005/0101460 A1 | 5/2005 | Lobban |
| 2005/0107229 A1 | 5/2005 | Wickens |
| 2005/0113223 A1 | 5/2005 | Dovner et al. |
| 2005/0130814 A1 | 6/2005 | Nitta et al. |
| 2005/0143234 A1 | 6/2005 | Massey |
| 2005/0148433 A1 | 7/2005 | Wang et al. |
| 2005/0184148 A1 | 8/2005 | Perlman |
| 2005/0225971 A1 | 10/2005 | Melnik |
| 2005/0248713 A1 | 11/2005 | Hirosue et al. |
| 2006/0007709 A1 | 1/2006 | Yuen |
| 2006/0026882 A1 | 2/2006 | Miller |
| 2006/0034074 A1 | 2/2006 | Ko |
| 2006/0035751 A1 | 2/2006 | Blair |
| 2006/0094573 A1 | 5/2006 | Weck |
| 2006/0116253 A1 | 6/2006 | Nizam |
| 2006/0122035 A1 | 6/2006 | Felix |
| 2006/0128540 A1 | 6/2006 | Engle |
| 2006/0189417 A1 | 8/2006 | Evans |
| 2006/0211549 A1 | 9/2006 | Nohejl |
| 2006/0272230 A1 | 12/2006 | Elwood |
| 2007/0021280 A1 | 1/2007 | Tyree |
| 2007/0097676 A1 | 5/2007 | Chien |
| 2007/0179022 A1 | 8/2007 | Chen |
| 2007/0184953 A1 | 8/2007 | Luberski et al. |
| 2007/0197345 A1 | 8/2007 | Wallace et al. |
| 2007/0263388 A1 | 11/2007 | Lai et al. |
| 2007/0287618 A1 | 12/2007 | Verheem |
| 2008/0007005 A1 | 1/2008 | Hsiao |
| 2008/0064578 A1 | 3/2008 | Huang |
| 2008/0077455 A1 | 3/2008 | Gilboa |
| 2008/0139370 A1 | 6/2008 | Charnitski |
| 2008/0154161 A1 | 6/2008 | Abbott |
| 2008/0161175 A1 | 7/2008 | Ho |
| 2008/0167168 A1 | 7/2008 | Hurst |
| 2008/0200851 A1 | 8/2008 | Faussett |
| 2008/0207415 A1 | 8/2008 | Tsai |

(56) References Cited

U.S. PATENT DOCUMENTS

| | | |
|---|---|---|
| 2008/0218998 A1 | 9/2008 | Quest |
| 2008/0242517 A1 | 10/2008 | Webber et al. |
| 2008/0252017 A1 | 10/2008 | Rowan |
| 2008/0263928 A1 | 10/2008 | Potterfield |
| 2008/0287272 A1 | 11/2008 | Luckadue |
| 2009/0017946 A1 | 1/2009 | Nally |
| 2009/0023553 A1 | 1/2009 | Shim |
| 2009/0048526 A1* | 2/2009 | Aarts ............... A61B 5/02438 600/508 |
| 2009/0075781 A1 | 3/2009 | Schwarzberg et al. |
| 2009/0093327 A1 | 4/2009 | Maziarz et al. |
| 2009/0105050 A1 | 4/2009 | Mayo |
| 2009/0112137 A1 | 4/2009 | Lamore |
| 2009/0124464 A1 | 5/2009 | Kastelic |
| 2009/0156367 A1 | 6/2009 | Harris, Jr. et al. |
| 2009/0176526 A1 | 7/2009 | Altman |
| 2009/0176635 A1 | 7/2009 | Brinson |
| 2009/0190332 A1 | 7/2009 | Sharrah |
| 2009/0207701 A1* | 8/2009 | Jacques ............... G04G 17/083 368/205 |
| 2009/0209393 A1 | 8/2009 | Crater et al. |
| 2009/0227426 A1 | 9/2009 | Dubar |
| 2009/0233773 A1 | 9/2009 | Cardey |
| 2010/0048368 A1 | 2/2010 | Donofrio |
| 2010/0058837 A1 | 3/2010 | Quest |
| 2010/0081549 A1 | 4/2010 | Thompson |
| 2010/0130337 A1 | 5/2010 | Stewart |
| 2010/0145240 A1 | 6/2010 | Cromie |
| 2010/0210426 A1 | 8/2010 | Styopin |
| 2010/0231142 A1 | 9/2010 | Yoon |
| 2010/0304931 A1 | 12/2010 | Stumpf |
| 2011/0057488 A1 | 3/2011 | Marten |
| 2011/0087076 A1 | 4/2011 | Brynelsen et al. |
| 2011/0216533 A1 | 9/2011 | Bertken |
| 2011/0224059 A1 | 9/2011 | Crawley |
| 2011/0287904 A1 | 11/2011 | Morris |
| 2012/0055718 A1 | 3/2012 | Chen |
| 2012/0083669 A1 | 4/2012 | Abujbara |
| 2012/0115694 A1 | 5/2012 | Chen |
| 2012/0184414 A1 | 7/2012 | Osborn |
| 2012/0208678 A1 | 8/2012 | Knilans |
| 2012/0238409 A1 | 9/2012 | Halsey |
| 2012/0244997 A1 | 9/2012 | Thompson |
| 2012/0310125 A1 | 12/2012 | Hall |
| 2012/0315609 A1 | 12/2012 | Miller-Kovach et al. |
| 2012/0317167 A1 | 12/2012 | Rahman et al. |
| 2013/0045841 A1 | 2/2013 | Chen |
| 2013/0053228 A1 | 2/2013 | Winegar |
| 2013/0059703 A1 | 3/2013 | Calantoni |
| 2013/0116068 A1 | 5/2013 | Traynor |
| 2013/0123083 A1 | 5/2013 | Sip |
| 2013/0130875 A1 | 5/2013 | Chou |
| 2013/0203570 A1 | 8/2013 | Ravikumar |
| 2013/0337984 A1 | 12/2013 | Lung |
| 2014/0005003 A1 | 1/2014 | Howell |
| 2014/0099614 A1 | 4/2014 | Hu et al. |
| 2014/0156308 A1 | 6/2014 | Ohnemus et al. |
| 2014/0162859 A1 | 6/2014 | Cheng |
| 2014/0235373 A1 | 8/2014 | Palardis |
| 2014/0256525 A1 | 9/2014 | Kybun |
| 2014/0274611 A1 | 9/2014 | Rex |
| 2014/0283339 A1 | 9/2014 | Gallagher et al. |
| 2014/0350443 A1 | 11/2014 | Raines |
| 2014/0371036 A1 | 12/2014 | Ellis |
| 2014/0375465 A1* | 12/2014 | Fenuccio ............... G08B 5/36 340/691.1 |
| 2015/0141220 A1 | 5/2015 | Wargo |
| 2015/0212541 A1* | 7/2015 | Lu ............... G04G 17/02 361/679.03 |
| 2015/0277384 A1* | 10/2015 | Mankowski ............ G04G 21/04 368/10 |
| 2015/0297134 A1* | 10/2015 | Albert ............... A61B 5/681 600/384 |
| 2015/0329255 A1 | 11/2015 | Rzepecki |
| 2015/0366518 A1* | 12/2015 | Sampson ............. A61B 5/7221 600/301 |
| 2015/0367160 A1 | 12/2015 | Medina |
| 2016/0074274 A1 | 3/2016 | Mallory |
| 2016/0144290 A1 | 5/2016 | Foote |
| 2017/0124912 A1 | 5/2017 | Ashby et al. |
| 2017/0188668 A1 | 7/2017 | Watterson et al. |
| 2017/0266489 A1 | 9/2017 | Douglass et al. |
| 2017/0354842 A1 | 12/2017 | Boland et al. |
| 2018/0147440 A1 | 5/2018 | Lin |

* cited by examiner

SMART WATCH BAND

CROSS-REFERENCE TO RELATED APPLICATIONS

This application claims priority to U.S. Provisional Patent Application No. 62/249,819 filed on Nov. 2, 2015, which application is herein incorporated by reference for all that it discloses.

BACKGROUND

A pedometer is a wearable device that tracks the steps that a user takes over time. In some instances, the pedometer is attached to a person's belt or another location on the user's body or clothing. As the user takes a step, an accelerometer or pendulum integrated into the pedometer senses the user's movement associated with the step and increments a counter that tracks the number of steps. In addition to pedometers, other types of activity trackers can be worn around a user's wrist. Some of these activity trackers share similarities with the pedometer. For example, these activity trackers can count the movement of the user's arm as well as the movements that are related to the user's steps.

One type of activity tracker is disclosed in U.S. Pat. No. 6,675,041 issued to Elisabeth N. Dickinson. In this reference, an apparatus for tracking net consumption of calories by a user has an input to allow a user to enter the number of calories in food consumed by the user. The apparatus also includes a heart rate monitor and a timer. A processor in the apparatus can calculate the number of calories expended by the user in an exercise session based on the duration of the exercise session, as measured by the timer, and the intensity of the exercise session as measured by the apparatus. The apparatus may be provided as a light weight self-contained wrist wearable instrument. The apparatus simplifies tracking the expenditure of calories in exercise and makes it possible for the user to vary dietary constraints on calorie consumption in accordance with the amount of exercise in which the user has participated. Another type of activity tracker is described in U.S. Pat. No. 6,823,036 issued to Yu-yu Chen.

SUMMARY

In one embodiment, a band includes a display and at least one replaceable module.

The band may also include a rod that connects an end of the band to a watch.

An orientation of the display may be aligned with a length of the rod.

An orientation of the display may be transverse with a length of the rod.

The band may include a segmented portion and the at least one replaceable module may be at least one link of a plurality of links of the segmented portion. The plurality of links may include a first link, a second link adjacent to the first link, a pin that rotatably secures the first link to the second link, and a processor disposed in at least one of the first link and the second link.

The band may further include a battery incorporated into the at least one replaceable module.

The band may further include a transmitter incorporated into the at least one replaceable module.

The band may further include a watch connected to an end of the band where the transmitter communicates with the watch.

The band may include a processing unit, and the transmitter may communicate with a remote device in response to a command from the processing unit.

The band may further include memory incorporated into the at least one replaceable module.

The band may further include an accelerometer incorporated into the at least one replaceable module.

The band may further include an electrode incorporated into the at least one replaceable module.

The band may further include a sensor incorporated into the at least one replaceable module.

The display may be incorporated into the at least one replaceable module.

The pin may include an electrically conductive material that completes a circuit incorporating the first link and the second link.

The band may further include a protrusion connected to an end of the band. The protrusion may include a skin side that includes an electrically conductive surface that contacts a user's skin when worn by a user and a watch side that receives a detachable watch.

In one embodiment, a wrist band includes a display, at least one replaceable module, and a segmented portion, wherein the at least one replaceable module is at least one link of a plurality of links of the segmented portion. The plurality of links includes a first link, a second link adjacent to the first link, a pin that rotatably secures the first link to the second link, and a processor disposed in at least one of the first link and the second link.

The pin may include an electrically conductive material that completes a circuit incorporating the first link and the second link.

The band may further include a protrusion connected an end of the band. The protrusion may include a skin side that includes an electrically conductive surface that contacts a user's skin when worn by a user and a watch side that receives a detachable watch.

In one embodiment, a wrist band includes a display, and at least one replaceable module, a segmented portion, and the at least one replaceable module is at least one link of a plurality of links of the segmented portion. The plurality of links includes a first link, a second link adjacent to the first link, and a pin that rotatably secures the first link to the second link, and a processor disposed in at least one of the first link and the second link. The pin includes an electrically conductive material that completes a circuit incorporating the first link and the second link. A protrusion is connected to an end of the band. The protrusion includes a skin side that includes an electrically conductive surface that contacts a user's skin when worn by a user and a watch side that receives a detachable watch.

BRIEF DESCRIPTION OF THE DRAWINGS

The accompanying drawings illustrate various embodiments of the present apparatus and are a part of the specification. The illustrated embodiments are merely examples of the present apparatus and do not limit the scope thereof.

Throughout the drawings, identical reference numbers designate similar, but not necessarily identical, elements.

DETAILED DESCRIPTION

For purposes of this disclosure, the term "aligned" means parallel, substantially parallel, or forming an angle of less than 35.0 degrees. For purposes of this disclosure, the term "transverse" means perpendicular, substantially perpendicular, or forming an angle between 55.0 and 125.0 degrees. Also, for purposes of this disclosure, the term "length" means the longest dimension of an object. Also, for purposes of this disclosure, the term "width" means the dimension of an object from side to side. For the purposes of this disclosure, the term "above" generally means superjacent, substantially superjacent, or higher than another object although not directly overlying the object. Further, for purposes of this disclosure, the term "mechanical communication" generally refers to components being in direct physical contact with each other or being in indirect physical contact with each other movement of one component affect the position of the other.

Figure 1:
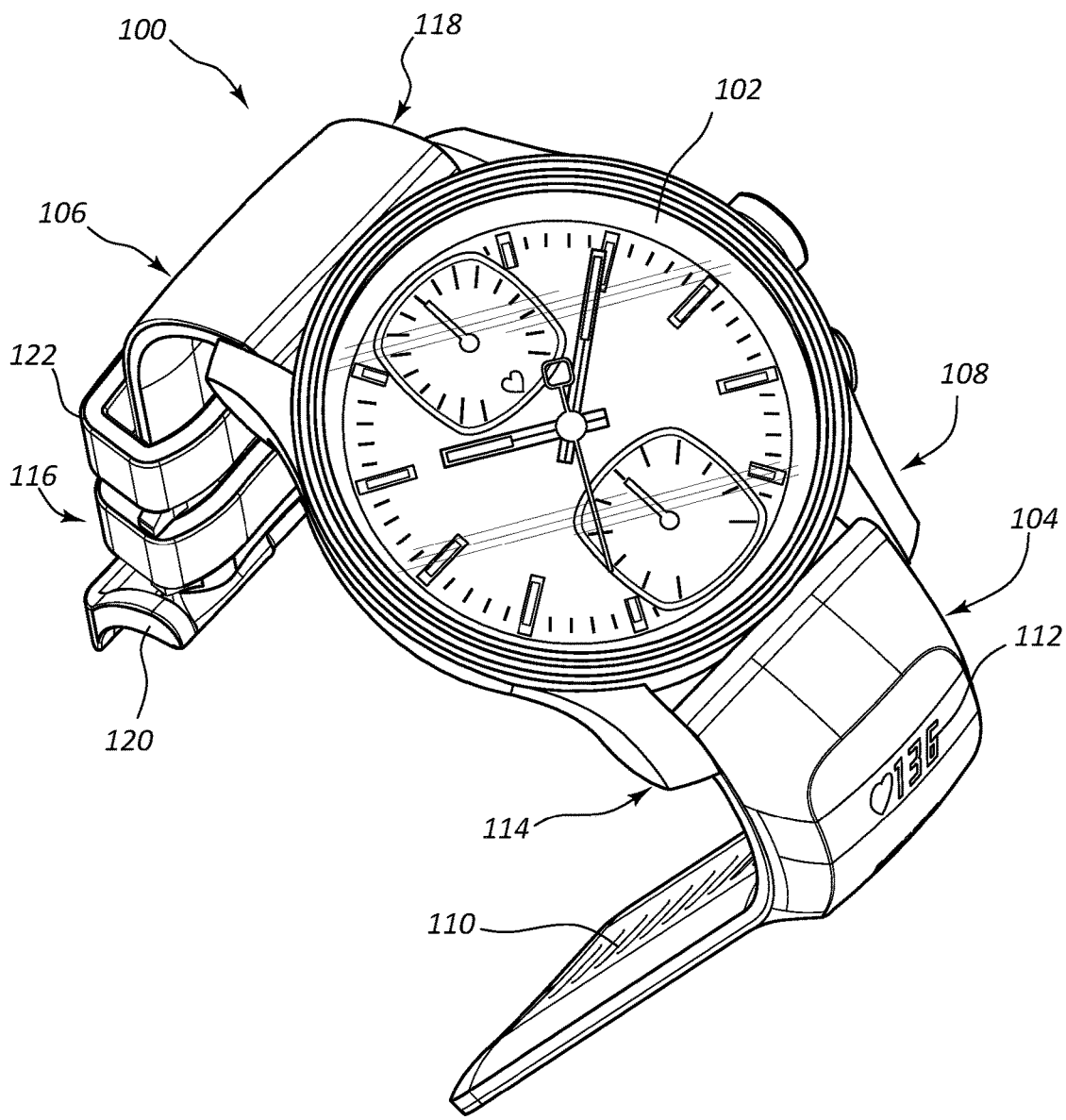
FIG. 1 illustrates a perspective view of an example of a wrist band in accordance with the present disclosure.

Particularly, with reference to the figures, FIG. 1 depicts an example of a wrist band 100 connected to a wrist watch 102. In this example, the wrist band has a first section 104 that is connected to a first side 106 of the wrist watch 102 at a first end 108 with a rod (not shown). The first section 104 includes multiple adjustment holes 110 and a display 112. In this example, the electrical components of the display 112 are contained within an increased cross sectional thickness 114 of the wrist band 100.

In some cases, the increased cross sectional thickness 114 exists because the display 112 is part of a replaceable module that can be detached from the wrist band 100. This replaceable module may be snapped into place on the wrist band 100 or otherwise attached to the wrist band 100. In some cases, the replaceable module includes components associated with the display, such as a processing unit, a transmitter, memory, input mechanisms, a speaker, a microphone, sensors, other types of components, or combinations thereof. But, some of these components may be integrated into other portions of the wrist band 100. When the replaceable module is connected to the wrist band 100, electrical leads and/or wires may electrical connect the replaceable module with the other electrical components of the wrist band 100.

The wrist band 100 also includes a second section 116 that is attached to a second side 118 of the wrist watch 102. The second section of the wrist band 100 includes a buckle 120 and loops 122. While this example has the display 112 on a different section of the wrist band 100 than the buckle 120 and the loops 122, the buckle 120 and the display 112 may be incorporated into the same section.

Any appropriate type of wrist watch 102 may be attached to the wrist band 100. In this example, a wrist watch 102 with a mechanical time tracking mechanism is attached to the wrist band 100.

Figure 2:
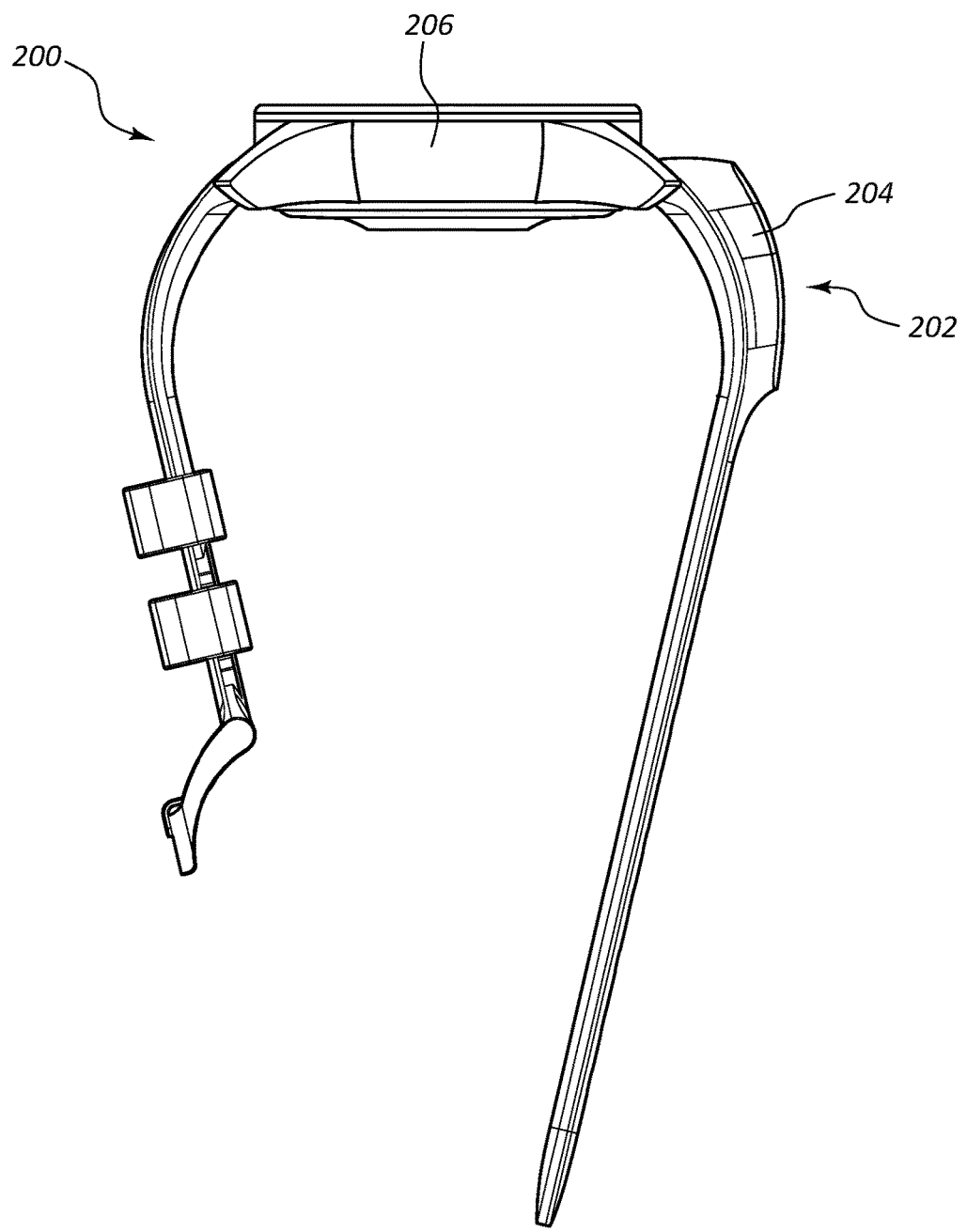
FIG. 2 illustrates a side view of an example of a wrist band in accordance with the present invention.

FIG. 2 depicts an example of the wrist band 200. In this example, the display 202 has a curved outer surface 204. Also, the display 202 is connected proximate the wrist watch 206. The wrist band 200 increases in thickness where the display 202 is attached. In this example, at least some of the electronics associated with gathering information to be presented in the display 202 are housed in the increased thickness.

Figure 3:
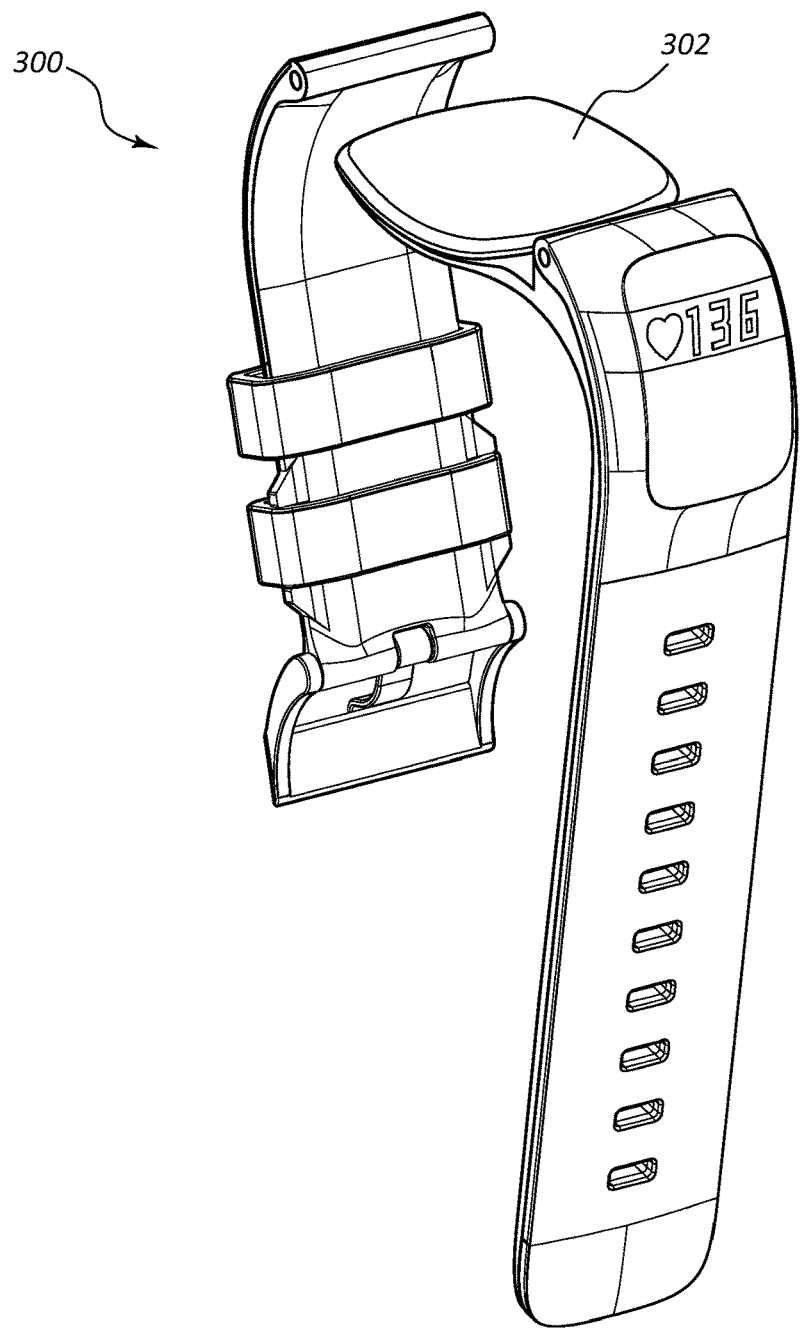
FIG. 3 illustrates a perspective view of an example of a wrist band in accordance with the present disclosure.

FIG. 3 depicts an example of the wrist band 300 with the wrist watch removed for illustrative purposes. In this example, a protrusion 302 extends from an inside surface 304 of the wrist band 300. The protrusion 302 forms a shelf. On one side of the protrusion 302, the protrusion 302 includes an electrically conductive material that can make contact with the user's skin when the user is wearing the wrist band 300. The other side of the protrusion may receive the wrist watch. In some cases, the other side of the protrusion includes an electrically insulating material to avoid interfering with the electrical signals that are sensed in the user's skin through the electrically conductive side of the protrusion.

The electrically conductive material may be in communication with a processing unit in another portion of the wrist band 300. The electrical signals sensed with the protrusion may be processed in the processing unit to determine physiological information about the user. For example, this kind of information may be used to determine the user's heart rate. In some cases, the bottom side of the protrusion includes multiple regions of electrically conductive materials that are spaced apart from each other to provide two different electrical contact points. This example allows the protrusion to sense an electrical potential. In other examples, the electrically conductive surface is a first skin contact that the user makes with an electrically conductive circuit incorporated into the wrist band 300. Another skin contact can be the user's finger that is pressed against another electrode elsewhere in the wrist band, completing the circuit. In yet another example, a second electrode may be incorporated into another portion of the wrist band 300. In some cases, there is just one skin contact in an electrical circuit with the wrist band and the user.

Figure 4:
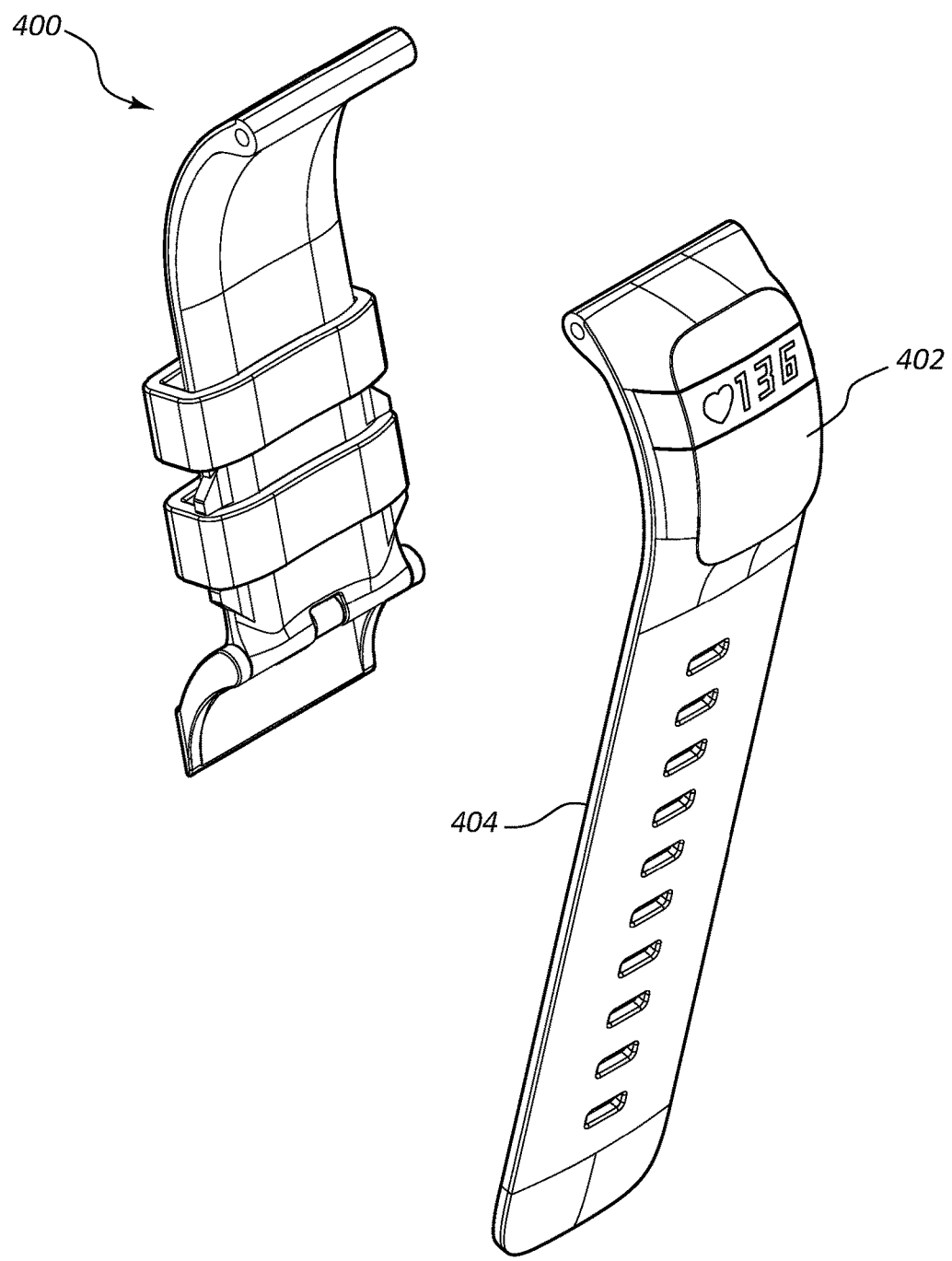
FIG. 4 illustrates a perspective view of an example of a wrist band in accordance with the present disclosure.

FIG. 4 is an example of the wrist band 400 without the wrist watch attached for illustrative purposes. In this example, no protrusions exists. However, the wrist band 300 may still acquire heart rate information to present in the display 402. For example, the wrist band 400 may be in communication with a remote heart rate monitoring device worn by the user during a workout. In other examples, electrodes are incorporated into the inside surface 404 of the wrist band 400 that sense the electrical properties of the user's skin.

Figure 5:
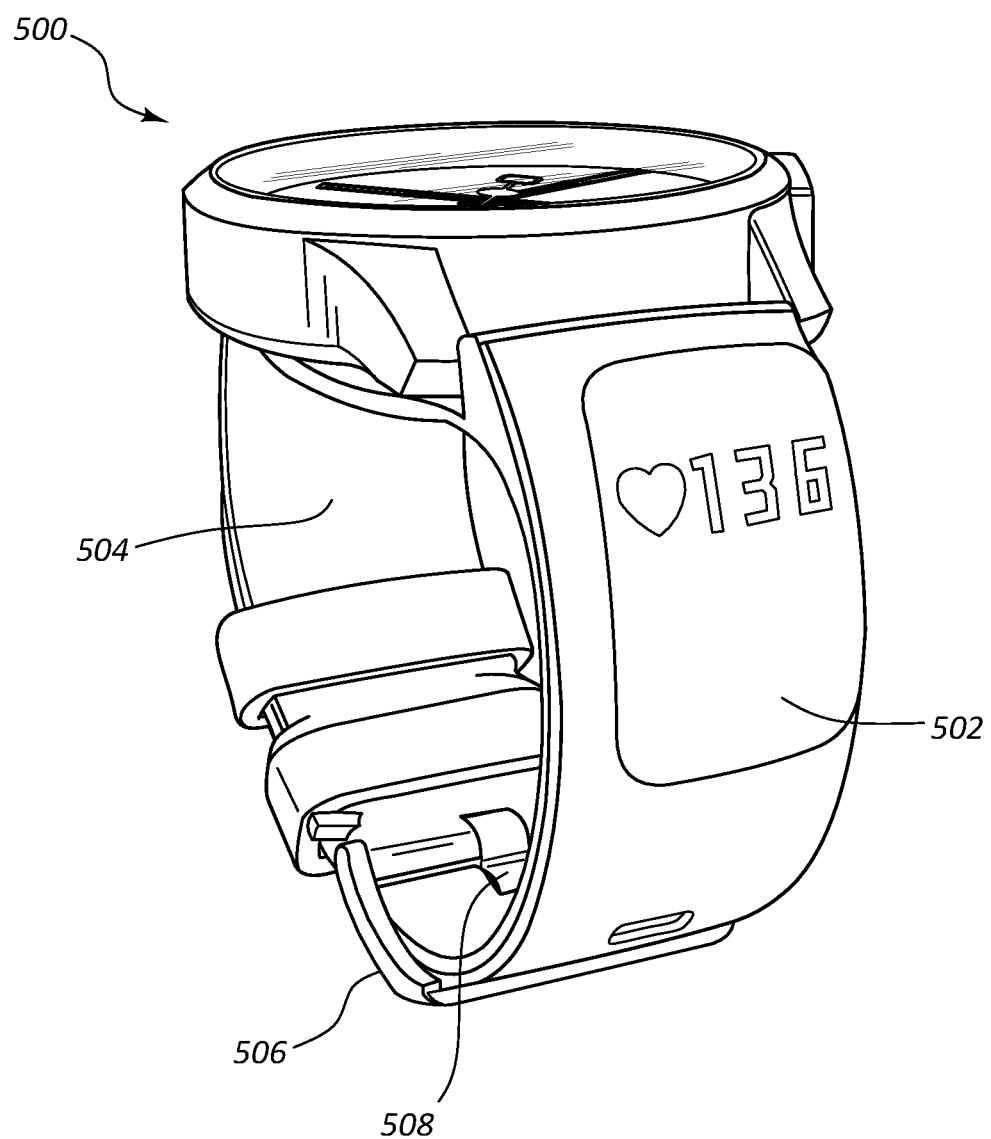
FIG. 5 illustrates a perspective view of an example of a wrist band in accordance with the present disclosure.

FIG. 5 is an example of the wrist band 500 where the first and second sections 502, 504 are attached. In this example, the buckle 506 of the second section 504 is fastened through the adjustment holes 508 in the first section 502.

Figure 6:
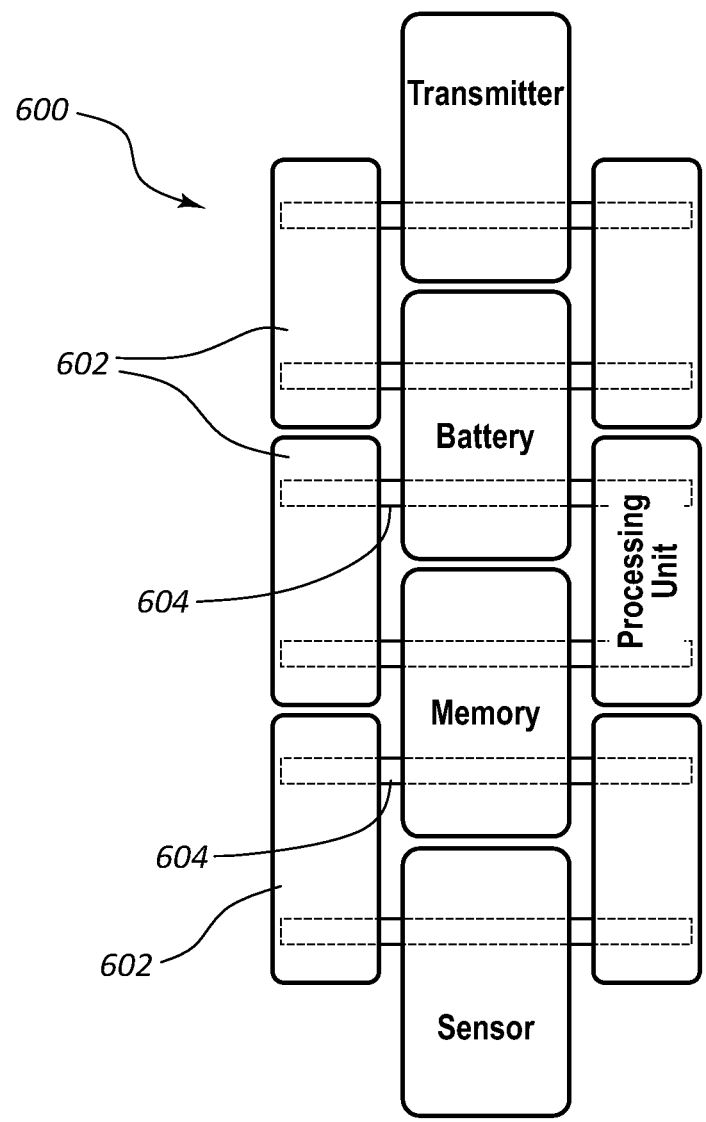
FIG. 6 illustrates a perspective view of an example of a wrist band in accordance with the present disclosure.

FIG. 6 depicts an example of a wrist band 600 that includes multiple links 602. At least some of the links 602 are removable and/or replaceable. At least some of the links 602 may include electronic components that can be used to gather, process, or present information to the user through the display or another communication mechanism. For example, at least one of the links may include a transmitter, a processing unit, memory, a sensor, an electrode, a battery, a charging port, a speaker, a microphone, an optical sensor, an audio sensor, a chemical sensor, a pressure gauge, another type of sensor, another type of device, or combinations thereof.

A first link and a second link may be connected to each other through a pin 604. In those situations where the first and second link include electronics, the pin 604 may be used to transmit power and/or data between the first and second links. In one embodiment, the pin 604 includes an electrically conductive material that is surrounded by an electrically insulating material. Signals (e.g. power and/or data) can be sent through the electrically conductive material while the outer electrically conductive material prevents the pin 604 from shorting out. The ends of the pin 604 may include regions that expose the electrically conductive material to the outside of the pin so that the electrically conductive material can make electrical connections with circuitry within the first and second links.

Figure 7:
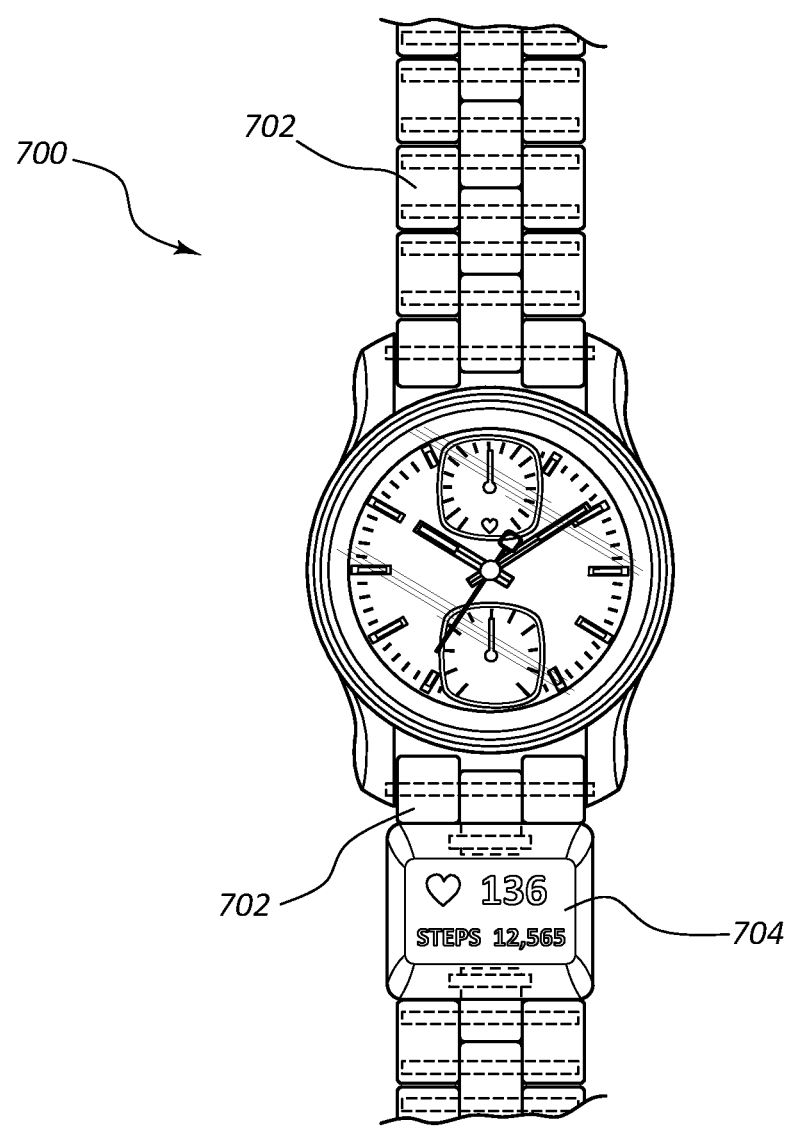
FIG. 7 illustrates a perspective view of an example of a wrist band in accordance with the present disclosure.
Figure 8:
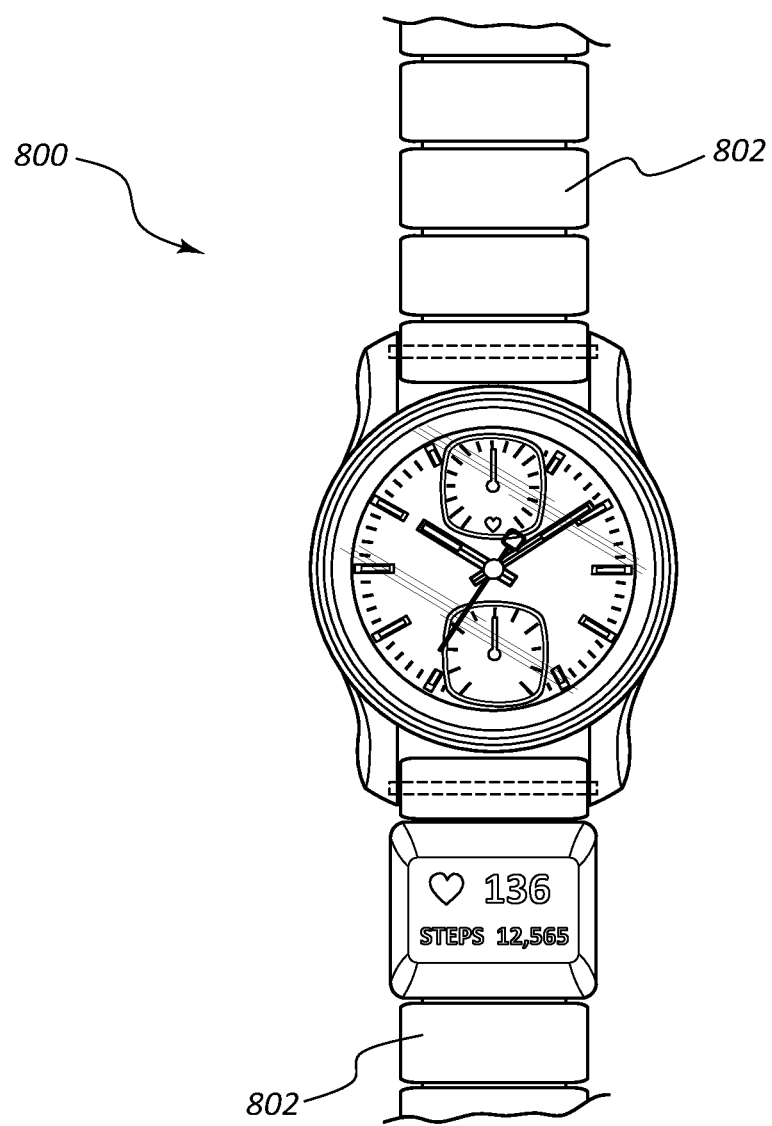
FIG. 8 illustrates a perspective view of an example of a wrist band in accordance with the present disclosure.

FIG. 7 depicts an example of a wrist band 700 that includes multiple links 702. A display 704 is attached to the links 702. In this example, each of the links 702 have a width that is shorter than the entire width of the wrist band 700. FIG. 8 depicts an example of the wrist band 800 made of links 802 where the links 802 are as wide as the width of the wrist band 800.

Figure 9:
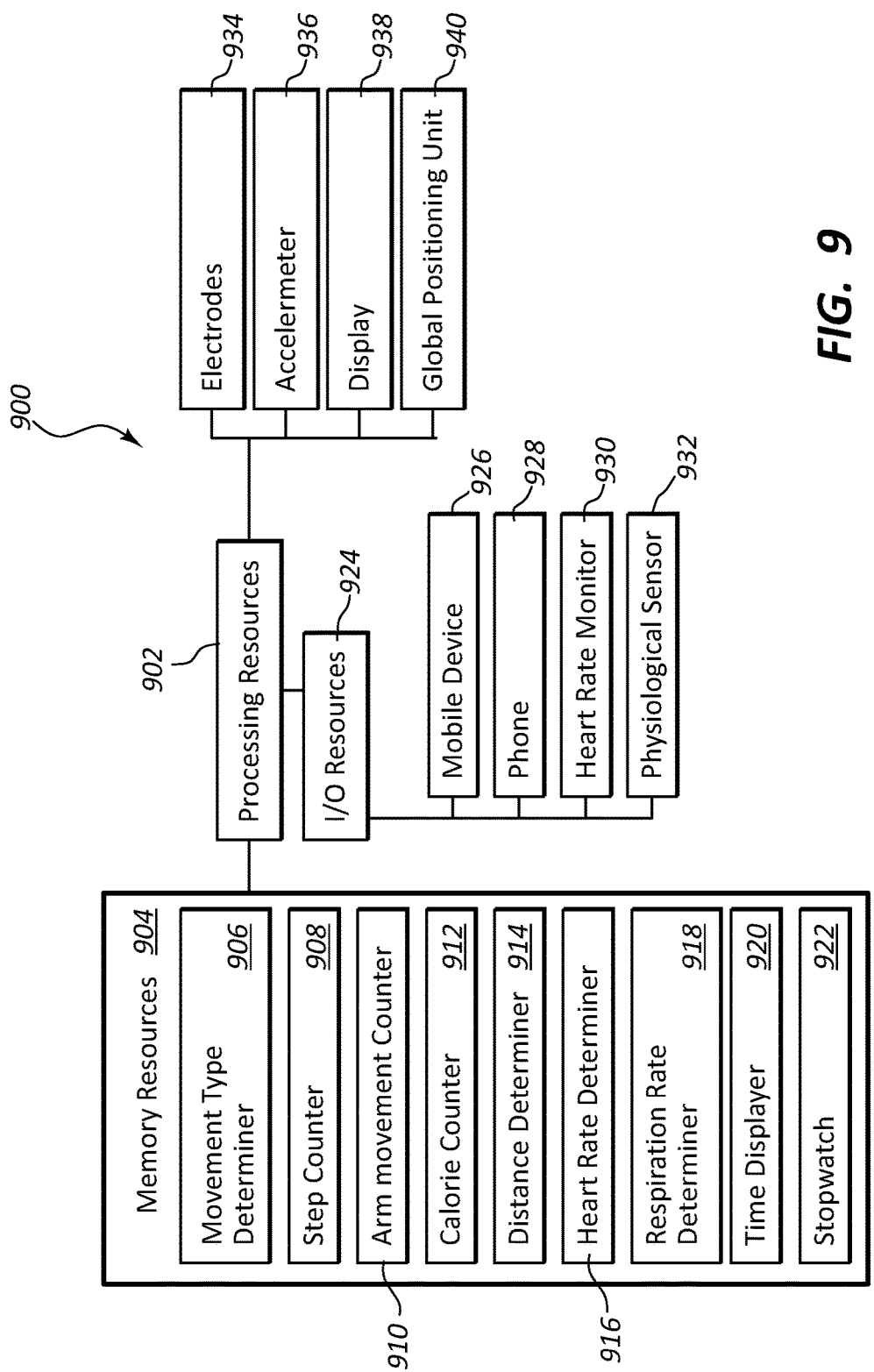
FIG. 9 illustrates a perspective view of an example of a system incorporated into a wrist band in accordance with the present disclosure.

FIG. 9 depicts an example of a system 900 incorporated into the wrist band. In this example, the system includes processing resources 902 in communication with memory resources 904. The memory resources 904 include a movement type determiner 906, a step counter 908, an arm movement counter 910, a calorie counter 912, a distance determiner 914, a heart rate determiner 916, a respiration rate determiner 918, a time displayer 920, a stopwatch 922, another type of programmed instruction, or combinations thereof. While the illustrated figure depicts the memory resources including specific types of programmed instructions, the memory resources may include any appropriate amount of programmed instructions and any appropriate type of programmed instructions. For example, the memory resources may include more or less programmed instructions than depicted in the illustrated figure. In other examples, the memory resources include more than just what is depicted in the illustrated example. In yet further examples, the memory resources may not include some of the programmed instructions depicted in the illustrated figure.

The processing resources 902 are also in communication with I/O resources 924. The I/O resources 924 may be in communication with a mobile device 926, a phone 928, a heart rate monitor 930, a physiological sensor 932, another type of remote device, or combinations thereof. While the illustrated figure depicts the I/O resources in communication with specific types of device, the I/O resources may be in communication with any appropriate number of device and any appropriate type of device. For example, the I/O resources may be in communication with more or fewer devices than depicted in the illustrated figure. In other examples, the I/O resources may be in communication with more than just what is depicted in the illustrated example. In yet further examples, the I/O resources may not be in communication with some of the devices depicted in the illustrated figure.

Also, the processing resources 902 may be in communication with components that are incorporated into the wrist band. These devices may include an electrode 934, an accelerometer 936, a display 938, a global positioning unit 940, other types of devices, or combinations thereof. While the illustrated figure depicts the processing resources in communication with specific types of devices, the processing resources may be in communication with any appropriate number of devices and any appropriate type of device. For example, the processing resources may be in communication with more or fewer devices than depicted in the illustrated figure. In other examples, the processing resources may be in communication with more than just what is depicted in the illustrated example. In yet further examples, the processing resources may not be in communication with some of the devices depicted in the illustrated figure.

Figure 10:
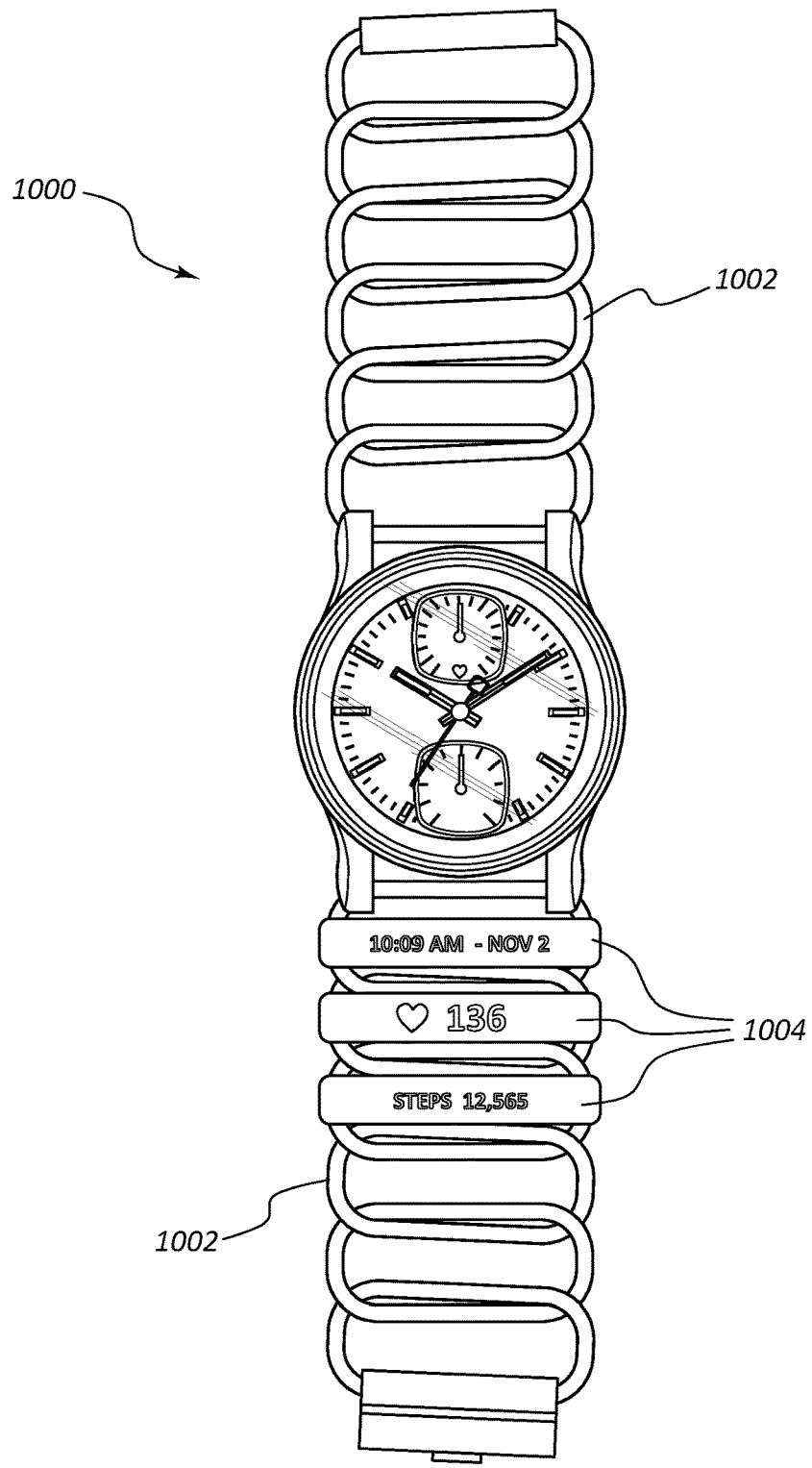
FIG. 10 depicts an example of a watch band where the band is made of multiple links.

FIG. 10 depicts an example of a watch band 1000 where the band is made of multiple links 1002. Displays 1004 are incorporated into the band 1000. Additional modules can be added to the band by replacing at least one of the links with a module. The module may communicate with the display's memory, batteries, and processing resources through wireless communication protocols. In other examples, the chain links include electrical contacts where power and/or data is transferred through the chain links between the display modules 1004 and the additional modules. These modules may provide additional functionality, such as modules for determining heart rate, blood oxygen levels, temperature, glucose levels, acceleration, location, movements, and so forth.

Figure 11:
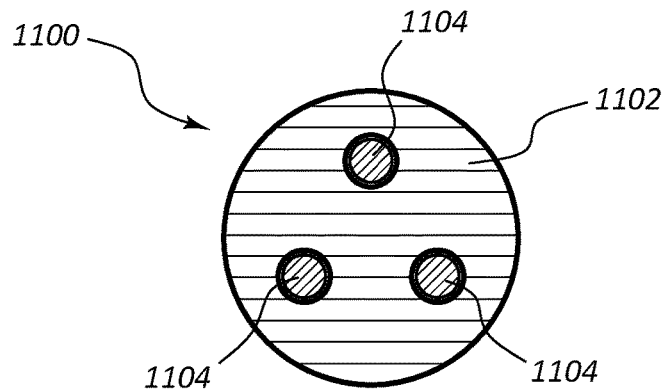
FIG. 11 depicts an example of a pin that connects links, such as the links depicted in FIGS. 6-7.

FIG. 11 depicts an example of a pin 1100 that connects links, such as the links depicted in FIGS. 6-7. In this example, the pin 1100 includes multiple electrical conductors 1104 housed in an electrical insulator 1102. The electrical insulator 1102 may be a plastic or another type of insulator, that prevents the conductors 1104 from shorting to one another. The conductors may transmit power and/or data between links. In some cases, one of the conductors may transmit power, another may transmit data, and another may provide a return path to complete the circuit. While this example is depicted with just three conductors 1104, any appropriate number of conductors may be incorporated into the pin 1100.

Figure 12:
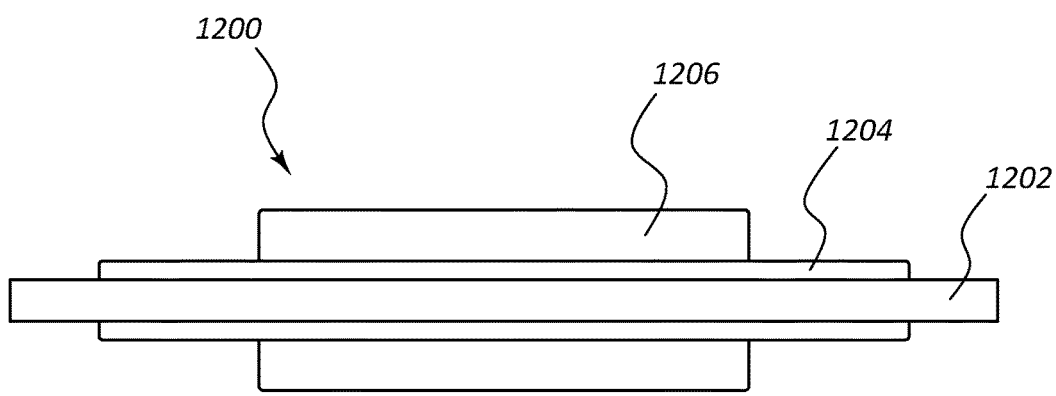
FIG. 12 depicts another example of a pin that connects links, such as the links depicted in FIGS. 6-7.

FIG. 12 depicts another example of a pin 1200 that connects links, such as the links depicted in FIGS. 6-7. In this example, the pin 1200 includes multiple electrical conductors 1202, 1204, 1206 that can transmit power and/or data between the links. In this example, the electrical conductors 1202, 1204, 1206 are concentric to one another and are separated a distance from each other with a dielectric material. The ends of the electrical conductors 1202, 1204, 1206 may be received in the links in a circular receptacle that makes an electrical connection between the electrical conductors 1202, 1204, 1206 and the receptacles. In some examples, the pin 1200 rotates with respect to one of the link and remains stationary with respect to the other link as the watch band moves. But, in other examples, the pin 1200 can move relative to each of the links as the watch band moves. In those examples where there is rotational movement between an end of the electrical conductors and the link's receptacle, the circular ends of the electrical conductors can rotate within the receptacles without breaking the electrical connection.

Figure 13:
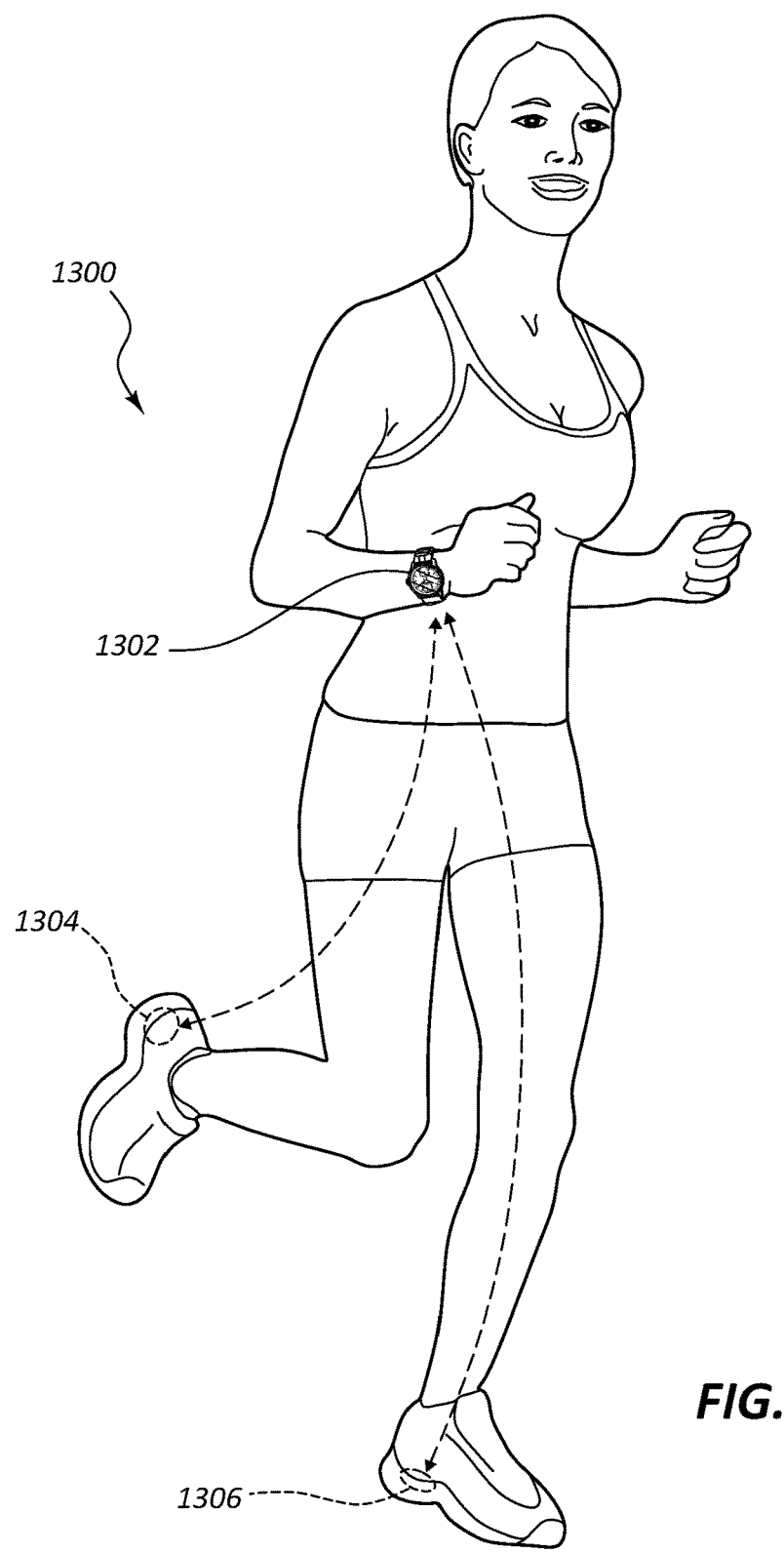
FIG. 13 depicts a system where the band is in communication with remote devices located in a shoe.

FIG. 13 depicts a system 1300 where the band 1302 is in communication with remote devices 1304, 1306 located in a shoe. The remote devices 1304, 1306 in the user's shoe may include an accelerometer, a sensor, or another type of device that counts the number of steps that the user takes. This remote device 1304, 1306 may send and receive messages from the band 1302.

INDUSTRIAL APPLICABILITY

In general, the invention disclosed herein may provide a wrist band that includes electronic features. This wrist band may be worn in conjunction with a wrist watch that also includes electronic features. In this example, the wrist watch and the wrist band may communicate with each other and coordinate with each other to present features in either the wrist watch's display or the band's display. In other examples, the wrist band is connected to a mechanical watch or another type of watch that does not have the ability to communicate information gathered through the wrist band. In this example, the information gathered with the wrist band may be presented in the display incorporated into the wrist band or that information may be sent to a remote device where the information is presented, stored, and/or further processed.

The display integrated into the wrist band may provide the user with helpful information that allows the user to make decisions about how active the user ought to be to reach fitness goals. The wrist watch display may show information like the estimated number of calories burned or other types of energy units intended to measure energy consumption. The wrist band may track the calories burned during the course of a workout and/or track the calories burned over a longer period of time.

The wrist band may include an accelerometer which can measure movements of the user's body to determine the number of steps taken by the user or measure other types of movement performed by the user. In some examples, the accelerometer is a multi-axis accelerometer that has the capability of distinguishing between stepping movements of the user, arm movements of the user, or other movements of the user. This type of accelerometer may record a pattern of vertical movements that occur at a substantially regular rate. The accelerometer or a processing device in communication with the accelerometer may determine that the recorded pattern corresponds with walking movements and that each of the vertical changes corresponds with a step. Further, the accelerometer or a processing device in communication with the accelerometer may have an ability to recognize patterns that correspond to arm movements or other types of body movements. As a result, the wrist band may have the capability of recognizing different types of body movements that can be used to determine the type of exercise performed by the user, the number of repetitions performed by the user, the calorie burn associated with these body movements, other data, and combinations thereof.

In some cases, the accelerometer may be used to determine the speed at which the user is moving. This may assist in determining the distance that the user is traveling during a workout or throughout the day. In other examples, the wrist band includes a global positioning system that identifies the user's location, which assists the wrist band in determining the speed and distance traveled by the user. The global positioning system may also assist the user in determining directions to desired locations. The user's stride length may also be determined with the accelerometer and/or the global positioning system.

In some examples, the wrist band can detect the user's heart rate. This may be accomplished by incorporating an electrode into the wrist band. The electrode may be located in any appropriate location along the wrist band. In one example, the electrode is incorporated into the band at the clasp that joins both sides of the wrist band together. In another example, the electrode is positioned adjacent an end of the band where the wrist band attaches to the wrist watch. In this example, the electrode may be incorporated into a protrusion that extends away from the wrist band. The protrusion may form a shelf with a first side that has an electrically conductive material. The electrically conductive material may be positioned against the user's skin so that protrusion can sense the electrical pulses transmitted through the user's body that regulate the user's heart rate. A second side of the protrusion may be opposite the first side and may be adjacent to the back side of the wrist watch. In some cases, the wrist watch may be detachable from the protrusion. In some cases, more than one electrode is attached and/or incorporated into the wrist band. Having at least two electrodes allows the wrist band to detect voltage differences, which can be used to assist in determining the heart rate. In some cases, the user can contact the electrode with his or her fingertip at a different location than where the electrode is contacting the skin about the user's wrist. Any appropriate type of electrical measurement may be read off of the internal electrically conductive pathway, such as a voltage differential, an electrical current, a resistance, or another type of electrical characteristic, or combinations thereof. While the above examples use the user's electrical characteristics to determine the user's heart rate, the user's heart rate may be determined using other types of physiological characteristics, such as capillary exchange, bioelectrical signals, blood pressure changes, blood volume change, acoustic signals, other types of signals, or combinations. These types of physiological characteristics may be measured with sensors that are incorporated into the user's wrist band.

The data gathered with the wrist band may be used to determine the number of calories burned by the user. The calorie count may be at least partially based on the body movements of the user that are track with the accelerometer. In this example, the wrist band may use any appropriate calculation to estimate a number of calories burned by the user in response to body movements. For example, the wrist band may assume that each movement of the user is a predetermined fraction of a calorie. In other examples, the wrist band associates a higher calorie count to certain kinds of movements, speeds, and repetitions. In this example, the wrist band may associate a higher calorie burn for leg movements than arm movements because leg movements move the entire weight of the body while arm movements may be moving just the weight of the arm.

Other sensors may be incorporated into the wrist band to aid in determining the number of calories burned by the user. For example, a heart rate monitor may be incorporated into the wrist band to determine how hard the user is working. Further, the wrist band may analyze the patterns from the accelerometer to determine how fast a user is walking. If the pattern reveals that a person is taking steps at a faster rate, the wrist band may associate a greater intensity of work being performed by the user and adjust the calorie count estimate accordingly.

Further, the wrist band may be in communication with other devices that are intended to measure other physiological parameters of the user that can be used as factors for determining the calorie count. For example, a thermometer may be positioned on the user to determine a temperature of the user. Likewise, an oxygen analyzer that measures the user's oxygen consumption may also be in communication with the wrist band. While these examples have been described with reference to specific devices and mechanisms that may be used in whole or in part for determining a calorie count, any appropriate mechanism for determining and/or estimating the user's calorie count may be used in accordance with the principles described in the present disclosure.

In some embodiments, the calorie count includes an estimated basal metabolic calorie count and an activity calorie count. To determine the basal metabolic calorie count, the wrist band may use information about the user. For example, the wrist band may request from the user information such as age, gender, height, weight, and other types of information that may be useful for determining the user's basal metabolic calorie count. This information may be gathered from other devices that store the user's personal information, such as a device that includes the user's profile. In other examples, this information may be retrieved from another type of remote storage device.

Other types of parameters may be tracked with the wrist band and/or presented in the display of the wrist band. In some examples, remote devices may gather physiological information about the user, which can be transmitted to the user. Other types of parameters that may be gathered and/or displayed with the wrist band include, but are not limited to, a breath rate, a distance traveled, a stopwatch, an arm movement count, another type of body movement count, a body temperature, a thermal characteristic of the body, a nutritional characteristic of the body, an electrical property of the body, a magnetic property of the body, a chemical property of the body, a pressure characteristic of the body, an average heart rate, a measured high heart rate, a measured low heart rate, a blood oxygen level, an ambient temperature, an atmospheric pressure, an ambient humidity, another atmospheric condition, an altitude, a current speed, a maximum measured speed, a sleep parameter, a fat loss parameter, a heart rate zone parameter, another type of characteristic of the body, or combinations thereof. Sensors for determining these types of parameters may be incorporated directly into the wrist band or these sensors may be in remote communication with the wrist band. Some of these remote sensors may be placed in the user's shoe, clothing, sport bra, chest strap, other wrist, hat, ear, leg, upper arm, another location in the clothing, another location on the user, or combinations thereof.

Further, the wrist band may include other features, such as email features, texting features, calendar feature, contact features, alarm features, camera features, weather features, alert features, map features, direction features, compass features, location features, social media features, fitness trainer features, other types of features, or combinations thereof.

In some examples, the wrist band can track at least one aspect about the user's sleep. For example, the wrist band may track the user's movements during sleep. The movements during sleep may be correlated with the sleep cycle in which the user is sleeping or be used to determine how deep the user is sleeping. The wrist band may use this information to determine how many calories the user is burning during sleep. Additionally or alternatively, the sleep information may be used to analyze sleep patterns of the user. For example, the sleep information can be used to inform the user that the user experiences a deeper sleep at certain times at night, which may help the user determine when to go to bed. Information collected by the wrist band during sleep may also be used to determine if the user snores, how hard the user snores, or determine another parameter about snoring. This information may be correlated with the user's activity during the day. In some cases, the wrist band may find a relationship between the amount of energy expended by the user during the day and the amount of snoring done by the user at night. In these examples, the wrist band may make a recommendation to the user for making changes to the user's sleep.

In some examples, the wrist band can detect the time that is takes a user to fall asleep, the duration of the user's sleep, the time that the user was in each sleep cycle, the time that the user was awake, the time that the user was restless, amount of oxygen consumed during sleep, oxygen saturation levels during sleep, other sleep parameters, or combinations thereof. These determinations may be made based on the user's movements, heart rate, respiratory rate, location, information detected with a microphone incorporated into the wrist band, other types of measurements, or combinations thereof. Further, the wrist band may recognize associations between the user's daily activity, the user's diet, other information recorded with the wrist band, or combinations thereof and the user's sleep. For example, the wrist band may recognize patterns that when the user drinks a stimulate (e.g. caffeine) before bed that the user's sleep experience changes. Further, the wrist band may analyze the physiological results of the user's sleep throughout the day or another time period following the user's sleep. For example, the user's heart rate, blood pressure, respiration, ability to lift heavy loads, other physiological results may be compared to the user's sleep the night before or the sleep history of the user over a time period including multiple nights to determine physiological changes/responses to the user's sleep experience.

The wrist band may include a combination of hardware and programmed instructions for executing the functions of the wrist band. In this example, the wrist band includes processing resources that are in communication with memory resources. Processing resources include at least one processor and other resources used to process the programmed instructions. The memory resources represent generally any memory capable of storing data such as programmed instructions or data structures used by the tracking system. Programmed instructions that may be stored in the memory resources include a movement type determiner, a step counter, an arm movement counter, a calorie counter, a distance determiner, a heart rate determiner, a respiration rate determiner, a time displayer, a stop watch, other programmed instructions, or combinations thereof. While this example has been described with specific types of programmed instructions, any appropriate type of programmed instructions may be used, which may be more or less than the programmed instructions listed above.

The memory resources include a computer readable storage medium that contains computer readable program code to cause tasks to be executed by the processing resources. The computer readable storage medium may be tangible and/or non-transitory storage medium. The computer readable storage medium may be any appropriate storage medium that is not a transmission storage medium. A non-exhaustive list of computer readable storage medium types includes non-volatile memory, volatile memory, random access memory, write only memory, flash memory, electrically erasable program read only memory, magnetic storage media, other types of memory, or combinations thereof.

The movement type determiner represents programmed instructions that, when executed, cause the processing resources to determine the type of movement executed by the user based on the outputs from the accelerometer. If the movement type determiner classifies a movement as a stepping movement, the processing resources can cause the step counter to increase to reflect the number of steps taken by the user. Likewise, if the movement type determiner classifies a movement as an arm movement, the processing resources can cause the arm movement counter to increase to reflect the number of arm movements executed by the user. In some examples, the movement type determiner can classify the movements as other types of movements, such as back movements, jumping movements, abdominal movements, core movements, other types of movements, or combinations thereof.

The calorie counter represents programmed instructions that, when executed, cause the processing resources to count the number of calories burned by the user. The calories counter may draw from the step counter, the arm movement counter, or another type of counter to determine the calorie count. Additionally, the calorie counter may also draw from a library to ascertain some of the variables used to calculate the calories burned, such as an age parameter, a weight parameter a gender parameter, another type of parameter, or combinations thereof. Further, the calorie counter may also draw from an output of the pulse rate determiner.

The distance determiner represents programmed instructions that, when executed, cause the processing resources to determine a distance traveled by the user. In some examples, the distance determiner obtains information from a global positioning unit to determine, at least in part, the distance traveled by the user. In other examples, the distance determiner obtains information from the step counter and information from a local or remote library. This information from the library may include a walking stride parameter and/or a running stride parameter specific to the user. The distance determiner may determine, based on output from the accelerometer, whether the user is running or walking and collect the steps taken by the user. In this example, the distance determiner may multiply the appropriate stride with the number of counts to determine a distance traveled.

The heart rate determiner represents programmed instructions that, when executed, cause the processing resources to count the number of beats measured from the user's pulse over a predetermined period of time with a pulse detector. The pulse rate determiner represents programmed instructions that, when executed, cause the processing resources to determine the pulse rate based on the pulse count measured with the pulse counter.

The respiration rate determiner may represent programmed instructions that, when executed, cause the processing resources to determine the respiration rate of the user. In some examples, the respiration rate is determined by receiving a signal from a remote device that records the user's respirations. The remote device may include a device that measures the user's diaphragm movements or measures the user's gas exchange during the user's breaths.

The wrist band may also include a time display that the user can view from the side of the user's wrist. Additionally, the wrist band can include a stopwatch function that allows the user to measure specific time periods associated with his or her workout or another type of event.

Further, the memory resources may be part of an installation package to be downloaded to the wrist band. In response to installing the installation package, the programmed instructions of the memory resources may be downloaded from the installation package's source, such as a portable medium, a server, a remote network location, another location, or combinations thereof. Portable memory media that are compatible with the principles described herein include DVDs, CDs, flash memory, portable disks, magnetic disks, optical disks, other forms of portable memory, or combinations thereof. In other examples, the program instructions are already installed in the wrist band. Here, the memory resources can include integrated memory such as a hard drive, a solid state hard drive, or the like.

The processing resources may be in communication with input/output (I/O) resources. Such I/O resources may include a transmitter that communicates with remote computing devices. In some examples, the remote computing devices send information to the I/O resources. But, in other examples, the I/O resources send information to the remote computing devices.

Any appropriate type of transmitter may be used in accordance with the principles described in the present disclosure. For example, the transmitter may be a radio transmitter, an optical transmitter, an acoustic transmitter, an antenna, another type of transmitter, or combinations thereof. Additional, any appropriate type of remote computing device may be in communication with the I/O resources, such as a mobile device, a phone, a wearable computing device, a heart rate monitor, a physiological sensor, a global positioning unit, a fitness tracking device, a fitness accessory, a digital device, another type of remote computing device, or combinations thereof.

The fitness tracking device may be a remote server or a cloud based device that stores fitness data about the user. For example, the fitness tracking device may include a user profile that includes the user's age, weight, height, gender, running stride, walking stride, other types of personal data, or combinations thereof. Further, the fitness tracking device may include the historical activities of the user. For example, the fitness tracking device may include data about the workouts that the user has performed over time, the number of calories burned, the distance run, the user's movement count, the user's historical heart rate, the amount of weight lifted, the number of lift repetitions, other types of fitness data, sleep data, nutrition data, medical condition data, other types of data, or combinations thereof. The fitness tracking device may be wired or wirelessly accessible to the user over the internet. As a result, the user may access this information through his or her mobile device, electronic tablet, laptop, desktop, smart phone, other type of device, or combinations thereof. In this manner, the user can retrieve historical information about his or her workout. In some examples, the user has an option to share at least some of his or her fitness data with friends that also use a fitness tracking program associated with the fitness tracking device. In this example, the user can remotely compete with friends and family in athletic activities. An example of a fitness tracking program that may be associated with the fitness tracking device is the iFit program, which can be found at www.ifit.com (last visited Apr. 25, 2014). The iFit program is available through ICON Health and Fitness, Inc. located in Logan, Utah, U.S.A.

In some examples, the processing resources and the memory resources are located within the wrist band. The memory resources may be part of the band's main memory, caches, registers, non-volatile memory, or elsewhere in the band's memory hierarchy. Alternatively, the memory resources may be in communication with the processing resources over a network. In this example, some of the memory resources may be located in one of the remote computing devices. Further, the data structures, such as the library, may be accessed from a remote location over a network connection while the programmed instructions are located locally.

The band may be in communication with an accessory. Examples of these accessories may include pedometers, motion detectors, speedometers, blood pressure monitors, electrocardiogram electrodes, other types of electrodes, global positioning units, mobiles devices, smart phones, other watches worn by other users, CPAP machines, other types of sensors that measures a physiological parameter of a user, other types of accessories, or combinations thereof. This accessories may be used to communicate data to the wrist band that can be used to at least assist with determining the appropriate measurement to display. Further, the accessories may track information obtained from the wrist band. In some cases, this obtained information may transmit the data to a central location storage device, perform calculations, perform another task with the data, or combinations thereof.

In some cases, the user's personal information can be stored locally on the wrist band. In these examples, the information may be inputted into the band through an input mechanism (e.g. touch screen, button, dial, switch, microphone, etc.). In other examples, the information is inputted into another device and sent to the band. In this example, the user can input information into the mobile device and send it to the wrist band. The user can input the user's age, gender, weight, height, preferences, body composition, other types of user information, or combinations thereof. Further, the user may input user activity that was not recorded with the wrist band. For example, if the user ran for twenty minutes without wearing the wrist band, the user may input that activity into the mobile device and communicate that information to the wrist band. Also, the user may input the number of calories that he or she consumed and send that to the wrist band. In those examples where the wrist band tracks the number of calories burned by the user, the wrist band can track the net amount of calories based on the calories consumed by the user and the amount of energy expended by the user. To make this calculation, the wrist band may determine the number of calories that the user needs to maintain his or her body at rest.

In some examples, the user inputs the number of calories that the user calculates that he or she consumed into the mobile device. In other examples, the user inputs the types of food and their corresponding amounts to into the mobile device. In this situation, the mobile device may calculate, based on the user's input, the number of calories that the user consumed. Alternatively, the mobile device may send the user's eating information to the wrist band to determine the number of calories consumed.

The user may also view information collected by the wrist band or view calculations performed by the wrist band on the mobile device. In some examples, the screen of the mobile device is larger than the either of the first or second displays of the wrist band, so the user may desire to view at least some of the information collected and/or calculated by the wrist band on the mobile device's screen. In other examples, the mobile device may include a key pad that has more features or that are easier to manipulate than the input mechanisms of the wrist band, so the user may prefer to input data or otherwise modify data with the mobile device.

Also, in the illustrated example, the wrist band is a metal wrist band. But, any appropriate type of wrist band may be used in accordance with the principles described in the present disclosure. For example, a non-exhaustive list of wrist bands that may be used include leather bands, stainless steel bands, titanium bands, caoutchouc bands, textile bands, nylon bands, synthetic bands, gold bands, metal bands, silver bands, aluminum bands, mesh bands, expansion bands, silicone bands, Velcro bands, clasp bands, strap bands, other types of bands, or combinations thereof.

In one example, the wrist band may include multiple chain links that are connected to one another. Such a chain may have the appearance of charm bracelet. One of the chain links may include a display, processing resources, and the battery. The band may receive additional functionality by added chain links that include sensors, transmitters, and other types of modules with different types of functionality. These additional modules may replace at least some of the current links in the band. Examples of sensors may that may added in this style of bracelet include radiofrequency functionality, an ability to identify blood sugar levels, temperature, heart rate, acceleration, movement, oxygen level sensor, blood-pressure, location detection, global positioning systems, secondary three axis gyroscope, glucose monitoring, and so forth. These sensors or other types of sensors may be used to determine the user's activities, like eating, sleeping, exercising, and so forth. Knowing the user's activity may help the processing resources interpret the readings that the sensors are measuring. In other examples, the added modules may resemble charms that hang from the bracelet. In some situations, the user may initially purchase the bracelet with standard features. But, later on, the user may purchase additional link modules that increase the bracelet's functionality.

In some examples, the modules in the chain bracelet models may be in wireless communication with each other. In yet other examples, the chain links provide an electrical contact for data and/or power transmission.

Any appropriate type of wrist watch may be connected to the wrist band. Thus, the wrist watch may be a digital wrist watch, a mechanical wrist watch, or combinations thereof. The wrist watch may include a mechanical counting mechanism, an electronic counting mechanism, or another type of counting mechanism. In some examples, the wrist watch is in communication with a remote computing device that tracks the time of day and conveys time information to the wrist watch. One benefit of the present wrist band system is that a user may use their current wrist watch, and incorporate the present wrist band to convert their wrist watch to a smart wrist watch, merely by changing out the wrist band.

Further, the wrist watch may be any appropriate size and/or shape. Compatible shapes may include generally circular shapes, generally rectangular shapes, generally square shapes, generally triangular shapes, generally star shapes, generally polygonal shapes, other shapes, or combinations thereof.

In some cases, the wrist band includes a first display that may be viewed at a different angle than the display of the wrist watch. This display may be secured to the portion of the wrist band that faces the user when the wrist band is secured to the user's wrist. The wrist band display may have a different look and feel than the display of the wrist watch. In some examples, the wrist band is connected to the wrist watch at an end of the band with a rod, however any appropriate alternative connection system may also be used. The orientation of the band's display may align with the rod's length. But, in other examples, the orientation of the band's display is transverse the rod's length. In yet other examples, the orientation of the screen changes based on input from the wrist band's accelerometer. For example, as the user changes the orientation of his or her arm, the orientation of the display screen may change so that the display appears in an orientation that is convenient for the user.

The band's display may turn off due to lack of interaction by the user. In some examples, the band may determine, based on accelerometer input or input from other sensors, that the user's arm that carries the watch is at the user's side. In this situation, the display screen may turn off to conserve the band's energy.

The wrist band may include removable modules. For example, the display screen may be held in a housing forming part of the wrist band, and be detachable from the wrist band. As the display screen is attached to the wrist band, the display electrical connects with the other components of the wrist band so that the display can receive instructions from the processing resources. In some examples, the display can be snap into and out of the wrist band. Circuit connectors may be incorporated into the back side of the display that make an electrical connection with wires or leads in the wrist band. The removable display screen may be attached to the wrist band using any attachment system including, but in no way limited to, a rod, screw, or other fastener; an adhesive; magnetic attachment; an interference fit with the wrist band housing; and the like.

The other components of the wrist band may also be part of replaceable and/or removable modules. For example, processing resources, memory, a battery, another type of power source, a transmitter, a input mechanism, a microphone, a speaker, an accelerometer, a global positioning system, an electrode, a sensor, another component of the wrist band, or combinations thereof may be part of a removable and/or replaceable module. These modules may snap into the wrist band. In other examples, these modules may be screwed or otherwise fastened to the wrist band. In some cases, the modules may be secured to the wrist band with a pin, fastener, magnetic attraction, and the like.

Any appropriate type of removable module may be used. In some cases, the removable modules are links in the wrist band. The links may be secured to one another with pins. In these embodiments, the links may house different components of the wrist band's electrical components. For example, one of the links may be dedicated to memory, a processing unit, a microphone, an input mechanism, a transmitter, a battery, a speaker, an accelerometer, another type of sensor, an electrode, or combinations thereof. In some cases, more than one link may be dedicated to each of the above mentioned devices. For example, more than one of the links may be dedicated to memory or processing resources. In other examples, at least one of the links is dedicated to more than one function.

Pins that connect the links to each other may include an electrically conductive material that may complete an electrical circuit when the pins are secured to both links. In one example, the outside of the pin includes an electrical insulator, which prevents the electrical circuit from shorting out if the outside of the pin comes into electrical contact with another electrical conductor. The inside of the pin may include an electrically conductive material that becomes part of the electrical circuit when securing both the pins to each other. The pin may include an exposed region, where the electrical insulator is removed and the pin's electrically conductive material is exposed. The exposed region may touch electrical contacts in the links establishing an electrical connection between the pin and the internal components of the link.

In an alternative example, the electrically conductive material is not exposed to the outside of the pin. In this example, the exposed region is replaced with an inductive coupling. The inductive coupling may include an electrically insulating, but magnetically conductive material, such as ferrite. In this example, the inductive coupling converts the electrical signal from the links into a magnetic signal, which passes down the pin's internal electrically conductive material. At the other end of the pin, the electrical signal is again converted into a magnetic signal and passed to the link, where the signal is converted back into an electrical signal. While the electrical connection between the pins and the links has been described above with reference to specific types of connections, any appropriate type of electrical connection may be used in accordance to the principles described in the present disclosure.

In some situations, the pins include multiple conductors. In one example, the pin is hollow and houses a pair of twisted wires in the hollow cavity of the pin. In other examples, the pin includes an electrically insulating material in its center which holds the twisted pair in place. In alternative examples, the multiple conductors may be parallel conductors where one of the conductors carries power, another of the conductors is the return, and the remaining conductor is for carrying data. The pin may also include a coaxial cable. One benefit of a coaxial cable is that the ends of the coaxial cable can be rotary contact with receptacles in the links on both sides. Thus, the as links rotate as the watch band is moved, the electrical connections at the ends of the pin can be maintain without imparting fatigue into the conductors. In a similar example, the conductors may be incorporated into a tri-axial cable. The triaxle cable may include an electrically conducting core, with two electrically conductive and concentric shield spaced apart from each other and the core with a dielectric materials. One of these conductors may carry power, another one of the conductors may be a return line, and the final conductor may be for carrying data.

The wrist band may include an operating system that sends and receives text messages, phone calls, alerts, timers, calendaring events, emails, workout instructions, and so forth. Also, the wrist band may have the ability to play music or other types of downloadable programs, connect to the internet, recognize audio commands, covert speech to text, establish a wireless connection with other devices, control other devices through the wireless connection, provide real time directions and other types of navigation features, support other features, or combinations thereof. Further, the wrist band may have the ability to download applications, such as from the Apple store or another type of repository. In some cases, the battery may be a rechargeable battery. In this situation, the battery module may be removed from the wrist band and placed in a charger. In yet other examples, the battery module may be charged by induction or may include a receptacle that receives at least one prong of a plug-in. In this case, the rechargeable battery may be recharged without removing the battery module from the wrist band.

While the examples above have been described with reference to the band being a wrist watch, the band may be attached to any appropriate location on the user. For example, the band may be worn on the user's forearm, upper arm, neck, ankle, leg, forehead, other portion of the user's body, or combinations thereof. The principles described in the present disclosure may be applied to necklaces, bracelets, ankle bracelets, chains, other types of jewelry, other types of bands, or combinations thereof.

What is claimed is:

1. A band, comprising:
    a display;
    at least one replaceable module; and
    a protrusion connected to an end of the band, wherein the protrusion includes a skin side having an electrically conductive surface that contacts a user's skin when worn on a user, and a watch side that receives a detachable watch.

2. The band of claim 1, further comprising an input mechanism configured to input information into the at least one replaceable module.

3. The band of claim 1, wherein the at least one replaceable module has an increased cross sectional thickness relative to the band.

4. The band of claim 1, wherein the display has a curved surface.

5. The band of claim 1,
wherein the at least one replaceable module a transmitter incorporated into the at least one replaceable module.

6. The band of claim 1, further comprising a rod attached to an end of the band, wherein the rod connects the end of the band to a watch.

7. The band of claim 6, further comprising an accelerometer, wherein an orientation of the display changes based on input from the accelerometer.

8. The band of claim 1, further comprising a segmented portion, wherein the at least one replaceable module is at least one link of a plurality of links of the segmented portion;
wherein the plurality of links includes:
a first link;
a second link adjacent to the first link;
a pin that rotatably secures the first link to the second link; and
a processor disposed in at least one of the first link and the second link.

9. The band of claim 1, further comprising a battery incorporated into the at least one replaceable module.

10. The band of claim 5, wherein the transmitter communicates with a watch connected to the watch side.

11. The band of claim 5, further comprising a processing unit;
wherein the transmitter communicates with a remote device in response to a command from the processing unit.

12. The band of claim 1, further comprising memory incorporated into the at least one replaceable module.

13. The band of claim 1, further comprising an accelerometer incorporated into the at least one replaceable module.

14. The band of claim 1, further comprising an electrode incorporated into the at least one replaceable module.

15. The band of claim 1, further comprising a sensor incorporated into the at least one replaceable module.

16. The band of claim 1, wherein the display is incorporated into the at least one replaceable module.

17. The band of claim 1, further comprising a pin that includes an electrically conductive material that completes a circuit incorporating a first link and a second link.

18. A wrist band, comprising:
a display; and
at least one replaceable module;
a segmented portion wherein the at least one replaceable module is at least one link of a plurality of links of the segmented portion;
wherein the plurality of links includes:
a first link;
a second link adjacent to the first link; and
a pin that rotatably secures the first link to the second link, wherein the pin includes an electrically conductive material that completes a circuit incorporating the first link and the second link; and
a processor disposed in at least one of the first link and the second link.

19. The band of claim 18, further including a protrusion connected an end of the band, the protrusion including a skin side that includes:
an electrically conductive surface that contacts a user's skin when worn on a user; and
a watch side that receives a detachable watch.

20. The band of claim 18, wherein the electrically conductive material is surrounded by an electrically insulating material, an end of the pin exposing a portion of the electrically conductive material.

* * * * *